US007074557B2

(12) United States Patent
Osbourn et al.

(10) Patent No.: US 7,074,557 B2
(45) Date of Patent: Jul. 11, 2006

(54) RIBOSOME DISPLAY

(75) Inventors: Jane Osbourn, Cambridge (GB); Thor Holet, Frederikssund (DK)

(73) Assignee: Cambridge Antibody Technology Limited, Cambridge (GB)

( * ) Notice: Subject to any disclaimer, the term of this patent is extended or adjusted under 35 U.S.C. 154(b) by 149 days.

(21) Appl. No.: 09/817,661

(22) Filed: Mar. 26, 2001

(65) Prior Publication Data

US 2002/0076692 A1 Jun. 20, 2002

Related U.S. Application Data

(60) Provisional application No. 60/193,802, filed on Mar. 31, 2000.

(51) Int. Cl.
*C12Q 1/68* (2006.01)
(52) U.S. Cl. .............................. 435/6; 435/7.1
(58) Field of Classification Search .................... 435/4, 435/6, 7.1, 69.1
See application file for complete search history.

(56) References Cited

U.S. PATENT DOCUMENTS

| 5,658,754 | A | 8/1997 | Kawasaki |
| 5,677,124 | A | 10/1997 | DuBois et al. |
| 5,919,625 | A | 7/1999 | DuBois et al. |
| 5,939,262 | A | 8/1999 | Pasloske et al. |
| 6,214,982 | B1 | 4/2001 | Pasloske et al. |
| 6,399,307 | B1 | 6/2002 | Pasloske et al. |

FOREIGN PATENT DOCUMENTS

| WO | WO 94/06920 | | 3/1994 |
| WO | WO 94/10329 | | 5/1994 |
| WO | 95/11922 | | 5/1995 |
| WO | 98/00547 | | 1/1998 |
| WO | WO 98/00547 | * | 1/1998 |
| WO | WO 98/48008 | * | 10/1998 |
| WO | WO 98/54312 | | 12/1998 |
| WO | WO 99/11777 | | 3/1999 |
| WO | WO 99/58661 | | 11/1999 |

OTHER PUBLICATIONS

Landt, O.; Grunert, H.-P.; Hahn, U. "A general method for rapid site-directed mutagenesis using the polymerase chain reaction" Gene 1990, 96, 125-128.*
Soukhanov, et al. Eds. Webster's II New Riverside University Dictionary. Boston: The Riverside Publishing Company 1988, p. 815.*
Lindeskog et al., "Sequence Variation of Human Endogenous Retrovirus ERV9-Related Elements in an env Region Corresponding to an Immunosuppressive Peptide: Transcription in Normal and Neoplastic Cells," *Journal of Virology*, 67(2):1122-1126 (Feb. 1993).
Weaver et al., "Spleen Necrosis Virus *gag* Polyprotein Is Necessary for Particle Assembly and Release but Not for Proteolytic Processing," *Journal of Virology*, 64(6):2642-2652 (Jun. 1990).
Sleat et al., "Packaging of Recombinant RNA Molecules into Pseudovirus Particles Directed by the Origin-of-Assembly Sequence from Tobacco Mosaic Virus RNA," *Virology*, 155:299-308 (1986).
Sleat et al., "Selective recovery of foreign gene transcripts as virus-like particles in TMV-infected transgenic tobaccos," *Nucleic Acids Res.* 8:3127-3140 (1988).
Mattheakis et al., "An *in vitro* polysome display system for identifying ligands from very large peptide libraries," *Proc. Natl. Acad. Sci. USA*, 91:9022-9026 (Sep. 1994).
Hwang et al., "Expression of tobacco mosaic virus coat protein and assembly of pseudovirus particles in *Escherichia coli,*" *Proc. Natl. Acad. Sci. USA*, 91:9067-9071 (Sep. 1994).
Hanes et al., "Ribosome display efficiently selects and evolves high-affinity antibodies *in vitro* from immune libraries," *Proc. Natl. Acad. Sci. USA*, 95:14130-14135 (Nov. 1995).
Hanes et al., "*In vitro* selection and evolution of functional proteins by using ribosome display," *Proc. Natl. Acad. Sci. USA*, 94:4937-4942 (May 1997).
Gersuk et al., "High-Affinity Peptide Ligands to Prostate-Specific Antigen Identified by Polysome Selection," *Biochem. Biophys. Res. Comm.*, 232:578-582 (1997).
Hoffmueller et al., "*In vitro* Evolution and Selection of Proteins: Ribosome Display for Larger Libraries," *Angew. Chem. Int. Ed.* 23:3241-3243 (1998).
Roberts, "Totally *in vitro* protein selection using mRNA-protein fusion and ribosome display," *Curr. Opin. Biotech.*, 3:268-273 (1999).

(Continued)

*Primary Examiner*—Andrew Wang
*Assistant Examiner*—Jon D. Epperson
(74) *Attorney, Agent, or Firm*—Klarquist Sparkman, LLP

(57) ABSTRACT

The use in a ribosome display system for selection of a specific binding pair member (e.g. antibody molecule) able to bind a complementary specific binding pair member (e.g. antigen) of encapsidating specific binding member/ribosome complexes in a viral coat, optionally in combination with incorporation of an Midvariant RNA template and optionally one or more other improvements selected from: a glycine-serine tether, protein disulphide isomerase, protein disulphide isomerase in combination with oxidized and reduced glutathione at a ratio of between 1:1 and 10:1, addition of oxidized and reduced glutathione at a ratio of between 1:1 and 10:1 after 30 minutes of in vitro translation; blocking with heparin during selection.

17 Claims, 10 Drawing Sheets

OTHER PUBLICATIONS

Amstutz et al., "*In vitro* display technologies: novel developments and applications," *Curr.Opin. Biotech*. 12:400-405 (2001).

Hwang et al., "Expression of tobacco mosaic virus coat protein and assembly of pseudovirus particles in *Escherichia coli*," *Proc. Natl. Acad. Sci. USA*, vol. 91, pp. 9067-9071 (1994).

Hanes et al., "Comparison of *Escherichia coli* and rabbit reticulocyte ribosome display systems," *FEBS Letters*, 450:105-110 (1999).

Makeyev et al., "Cell-free immunology: construction and in vitro expression of a PCR-based library encoding a single-chain antibody repertoire," *FEBS Letters*, 444:177-180 (1999).

* cited by examiner

Figure 2B

------AA TTC TAA TAC GAC TCA CTA TAG GGA GAG CAC TTC TGA TCC AGT CCG ACT
GAG AAG GAA GGC CCA GCC ATC TGC AGT ACG CGG CCG CA CAT CAT CAT CAC CAT CAC
GGG GCC GCA CAA AAA CTC ATC TCA GAA GAG GAT CTG AAT GGC CGC
GGCAGCGGGTCCGGCTCTGGGAGCGGATCCGGCTCTCTGGGCTCCGGATCGGGCTCCGGATCAGGCTC
GGGCTCCGGATCTGGATCGGGCTCCGGATCCGGGTCGGGCTCCGGATGGGGTCGGGTTCGGGATCA
TACCCGTATGACGTGCCGGATTACGCA-----

RIBOSOME DISPLAY

CROSS REFERENCE TO RELATED APPLICATION

This application claims the benefit of U.S. Provisional Application No. 60/193,802 filed Mar. 31, 2000.

The present invention relates to ribosome display and is based in various aspects on various improvements made by the present inventors which individually or in combination provide advantages over existing techniques.

Ribosome/polysome selection involves construction of nucleic acid libraries, screening for binding, and identification of binding entities of interest. The library is made by synthesising a DNA pool of diverse sequences that are then transcribed to produce a pool of mRNAs. In vitro translation is used to generate the encoded polypeptides or proteins displayed on the ribosomes, and desirable binding interactions are selected using immobilised target antigen. mRNA encoding the binding entities can be recovered and used to make cDNA, which can then be amplified and the process may be repeated to enrich the population for genes encoding binders. The selected proteins may later be identified by cloning individual coding sequences and DNA sequencing.

Recovery of mRNA from polysome complexes was first reported in 1973 in a paper describing a protocol to capture mRNA coding for a mouse immunoglobulin L-chain using antibodies and immobilised oligothymidine (Schechter (1973) PNAS USA 70, 2256–2260). Improvements to the polysome immunoprecipitation protocols were made by Payvar and Schimke (Eur. J. Biochem. (1979) 101, 271–282) and cDNA clones for the heavy chain of HLA-DR antigens were obtained after immunoprecipitation of polysomes using a monoclonal antibody (PNAS USA (1982) 79, 1844–1848). Production of libraries of antibodies by ribosome display was proposed and patented by Kawasaki (U.S. Pat. Nos. 5,643,768 and 5,658,754).

There have been various examples of the use of ribosome display using either eukaryotic or prokaryotic translation systems. The first demonstration of selection of peptide ligands that using an *E. coli* extract was by Mattheakis et al., (PNAS USA (1994) 91, 9022–9026 and Methods Enzymol (1996) 267, 195–207). This group demonstrated selection of peptide ligands that are similar to known peptides epitopes of a given antibody, using the antibody as a selection substrate. High-affinity peptide ligands which bind prostate-specific antigen have been identified using polysome selection from peptide libraries using a wheat germ extract translation system (Gersuk et al., (1997) Biotech and Biophys. Res. Com. 232, 578–582). The selection of functional-antibody fragments was reported using an *E. coli* translation system designed for increased yield of ternary complexes and allowing disulphide bond formation (Hanes and Pluckthun, PNAS USA (1997) 94, 4937–4942). This experimental set up has subsequently been used to select antibodies from a murine library, and it was shown that affinity maturation occurs during the selection due to the combined effect of PCR errors and selection. A scFv fragment with a dissociation constant of about $10^{-11}$M was obtained (Hanes et al., PNAS USA (1998) 95, 14130–50). Enrichment for specific of antibodies from mixed populations using rabbit reticulyocyte lysate extracts has also been demonstrated (He and Taussig (1997) NAR, 5132–5234).

The technology as reported in the literature has not been applied to the selection of antibodies that bind to a target antigen directly from a naive library. To date the libraries created have been generated using material from mice immunised with a particular antigen and such libraries have formed the basis of affinity selection procedures. A number of factors may contribute to the difficulty in generating antibodies directly from naive libraries. These include the following.

(1) The generation of polysomes using a ribosome display library will result in a number of ribosomes translating the same mRNA, only one of which will be able to completely translate the entire message. The remaining ribosomes will partially translate the message and stall since ribosome release from the end of the message does not occur in this system. This may result in the expression of partial polypeptide fragments that may not be capable of forming correct secondary and tertiary structures. These partially translated fragments may have exposed hydrophobic surfaces and as a result may be non-specifically sticky. The presence of partially translated polypeptide fragments in a selection system may result in the non-specific selection of partially translated fragments, and may reduce the efficiency of the selection process. The present inventors have generated populations of monosomes rather than polysomes, which by definition avoid the presence of partially translated protein. A single ribosome is recruited to a single mRNA molecule, so producing one full length displayed polypeptide per mRNA.

(2) Polypeptides may not be correctly folded in the in vitro translation system and hence not be able to correctly interact with their binding partner (e.g. antibody molecules may not be able to fold and interact correctly with antigen). Proteins fold through intermediate states that have exposed hydrophobic surfaces that have a tendency to aggregate. In addition, proteins can misfold by incorrect disulphide formation. It is thought that intramolecular disulphide bond formation may be the rate limiting step in the folding of some proteins. The process may involve thiol S—S interchange reactions in which incorrectly linked S—S bridges are replaced by native S—S bonds. It has also been shown that correctly S—S bonding in newly synthesised protein in rabbit reticulocyte lysates depends on the relative amounts of oxidised and reduced thiols (Kaderbhai and Austen 1985, Eur J. Biochem, 153, 167–178). The extent of correct S—S pairing is dependent on the amounts of GSSG added at the onset of translation and is also dependent on the rates at which thiol levels change during the translation phase. The inventors have provided an approach which can be used to achieve increased levels of correctly folded and therefore active antibody molecules (e.g. scFv) in eukaryotic ribosome display systems, employing protein disulphide isomerase (PDI).

(3) Naive libraries used as starting points for antigen selections should be highly diverse and incorporate various features including detection tags and tethers to avoid steric hindrance between the ribosome and the scFv and to allow efficient co-translational folding of the scFv. To date, antibody libraries generated for use in ribosome display selections have been produced from immunised mice and cloned into specifically designed ribosome display vectors (Hanes et al., PNAS USA 1998, 95: 14130–50). It has, however, also been shown that construction and in vitro expression of an antibody library presented as a population of PCR fragments, rather than cloned into a ribosome display expression vector, is possible (Makeyev et al., FEBS Letters 444 (1999) 177–180). Makeyev et al. describe generation of a scFv repertoire using PCR assembly of VH and VL gene segments with a linker fragment. The use of PCR assembly techniques to generate naive repertoires avoids the need for cloning and hence theoretically allows generation of very large libraries.

The present inventors have designed a novel cloning-independent PCR assembly strategy to generate ribosome display libraries containing features necessary for transcription and translation at the 3=end of the fragment, and using a DNA cassette approach to incorporate tether fragments at the 5=end of the construct. Very large libraries can be generated with a choice of tether cassette suitable to the particular library or application. Tethers fragments can be structured, non-structured, contain packaging or replication sequences, or be used as the basis for generation of affinity maturation libraries by extension of the tether into the polypeptide to be displayed. In this case a mutagenic oligonucleotide is designed to amplify the tether fragment along with the region of the polypeptide (e.g. VH CDR3 for a scFV molecule) which is to be targeted for mutation. The mutagenesis oligo should cover the region of mutation and also incorporate an anchor region upstream of the region of mutagenesis to allow efficient OCR assembly of the complete polypeptide tether construct. Examples of strategies for use of tether cassette are outlined in FIG. 1. The present inventors have designed a novel mutagenesis strategy that enables the mutagenesis steps to be incorporated into a ribosome display selection cycle. Selected mRNA may be subjected to mutagenesis, prior to RT-PCR, using a primer designed to target sequence encoding a particular region of the polypeptide or peptide (e.g. CDR of an antibody molecule). Following assembly and pull-through reactions, PCR products may then be used directly in the next round of selection, enabling isolation of binding molecules with improved binding capabilities at each stage. This may be used to mutagenise all the CDR=s of an antibody molecule. (FIGS. 7, 8 and 9 illustrate embodiments of this aspect of the present invention.)

(4) The RNA displayed in the ribosome display system is labile and prone to degradation. An RNase-free environment must be provided at all times during the selection procedure and preferably work must be carried out at 4□C. It is also a requirement that the antigen on which selections are being carried out is free of any RNase contamination and is highly purified. These constraints limit the applicability of ribosome display selection.

The present inventors have developed a method for encapsidating ribosome display RNA in a protein coat which greatly increases the stability of RNA over a range of temperatures, and renders it resistant to degradation to RNase.

In preferred embodiments, the protein used for encapsidation is tobacco mosaic virus (TMV) coat protein, but other plant or animal viral coat proteins may be employed.

Other plant or animal viral coat proteins may be employed. Various rod-shaped or bacilliform plant viruses have the ability to self assemble and these systems may be applied to provide packaging reagents for ribosome display libraries (Hull and Davies (1983) Genetic engineering with plant viruses and their potential as vectors In "Advances in Virus Research" (Lauffer and Maramorosch, eds) Vol. 28, 1–33. Academic Press, Orlando, Fla). Such viruses include any positive strand plant or animal RNA virus. Plant RNA viruses include, but are not limited to, members of the Tobamovirus, Potexvirus, Potyvirus, Tobravirus, Cucumovirus or Comovirus families. Animal viruses would include, but are not limited to, the Togaviridae, Flaviviridae, Picornaviridae and Caliviridae. Coat proteins derived from DNA viruses such as cauliflower mosaic virus may also be employed for encapsidating DNA or RNA, as may coat proteins or bacteriophage lambda (reviewed in "Principles of Gene Manipulation" Third edition (1985) Old and Primrose, Blackwell, Oxford).

Native TMV particles are extremely stable and retain infectivity for decades. Over 2100 copies of a 17.6 kDa coat protein fully protect the 6.4 kb single stranded RNA genome against degradation. TMV was employed in spontaneous self-assembly of multimeric biological structure in vitro (Butler and Klug 1971 Nature New Biol. 229, 47–50). TMV assembly is initiated by a specific interaction between a prefabricated (20 S) protein aggregate (the disk, or protohelix) and a stem-loop-structured RNA origin of assembly sequence (OAS) sequence, that is centred either 0.4kb or 0.9 kb from the 3=end of the genomic RNA (Zimmern and Wilson, 1976 FEBS Lett 71, 294–298). In addition to native TMV RNA, TMV coat protein has also been shown to package chimeric ssRNAs efficiently (Sleat et al., 1986, Virology 155, 299–308) in a length- and sequence-independent manner provided that a contiguous region of the loop 1 of the OAS sequence (genome co-ordinates 5444–5518) was present. This can occur in vitro, or in vivo in transgenic tobacco plants (Sleat et al., 1988, NAR 16, 3127–3140). Only ssRNA, not ssDNA can be packed by the coat protein. It has been suggested that the exceptional stability of TMV-like particles to proteases and RNases can be exploited to recover, store, and protect otherwise labile mRNA molecules to deliver them into plant or animal cells for subsequent cotranslational disassembly (Gallie et al., Science 236, 1122–1124).

The present inventors have now shown that it is possible to generate ribosome display libraries containing the a viral packaging OAS which can be encapsidated in viral coat protein, hence providing increased stability to the RNA. TMV is co-translationally disassembled in vivo (Wilson 1984, Virology, 137, 255–265) and in vitro. Encapsidated ribosome display RNA may also be co-translationally disassembled. It has also been demonstrated that the presence of translocating ribosomes present on the OAS-containing RNA do not completely inhibit RNA packaging. It appears that the RNA molecule is packaged in the 3= to 5=direction as far as the progressing ribosome, but eventually the packaging process is blocked by the advancing ribosome. Complete translation of the ribosome display mRNA may be allowed to generate the polypeptide mRNA ribosome complex prior to initiation of the packaging reaction to produce a fully encapsidated complex.

The inventors have additionally incorporated into ribosome display constructs and methods an RNA template known as Midvariant (MDV) RNA, enabling replication by Qβ replicase (Wu et al., PNAS, 1992, 89: 11769–73. This allows for exponential replication of a ribosome display library in vivo. For replication by Qβ replicase, the RNA template adopts a secondary structure to initiate recognition and replication. Brown et al, Biochemistry, 1995, 34:45, 14765–74 have shown two RNA binding sites on Qβ replicase.

BRIEF DESCRIPTION OF THE FIGURES

FIG. 2 illustrates a ribosome display construct according to an embodiment of the present invention:

FIG. 2B shows the sequence of the ribosome display construct of this embodiment of the present invention (within a pCU vector). The bold triplets show the SfiI, PstI and NotI restriction sites. The continuous stretch of bold shows the sequence encoding the tether. The key features of the construct of this embodiment of the present invention are a T7 promoter, ribosome binding site, Kozak consensus sequence, SfiI/PstI/NotI cloning sites, his tag, myc tag, gly-ser tether and HA tag.

Figure 1:
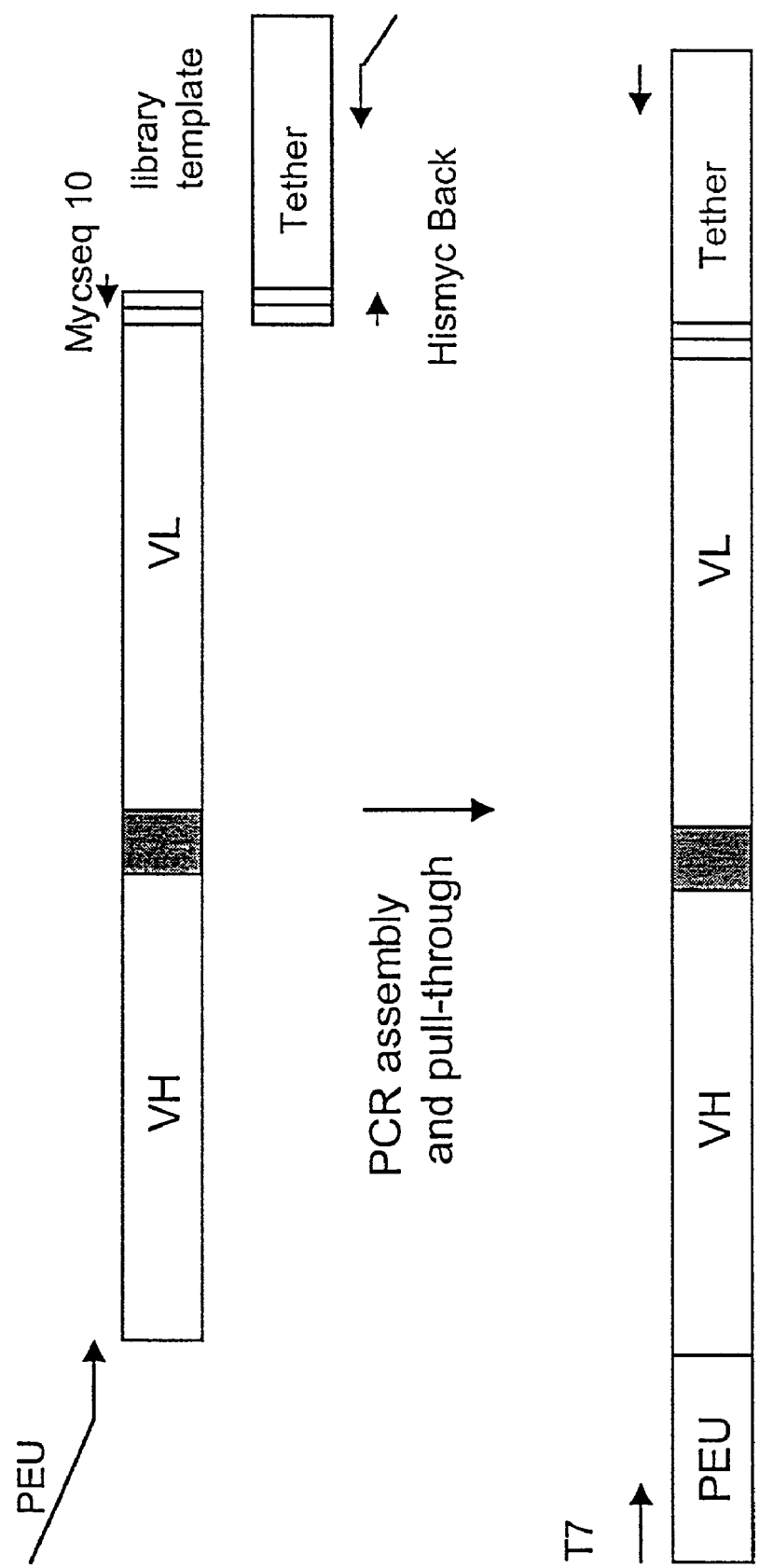
FIG. 1 illustrates a scheme for generation of a PCR assembled naive scFv repertoire in accordance with an embodiment of the present invention. Primers PEU, Mycseq 10 and Hismyc Back are as described in the text. In preferred embodiments of the invention, the tether is poly-glycineserine. In the assembled construct, PEU is the protein expression unit consisting of promoter, consensus sequence and ribosome binding site.

According to various aspects, the present invention provides the use of any one or more of the following features in a ribosome display system for selection of a specific binding pair member (e.g. antibody molecule) able to bind a complementary specific binding pair member (e.g. antigen):

(i) a glycine-serine tether, in a eukaryotic or prokaryotic system;
(ii) protein disulphide isomerase (PDI), in a eukaryotic system;
(iii) protein disulphide isomerase (PDI) in combination with oxidised and reduced glutathione at a ratio of between 1:1 and 10:1, in a eukaryotic or prokaryotic system;
(iv) addition of oxidised and reduced glutathione at a ratio of between 1:1 and 10:1 after 30 minutes of in vitro translation in a eukaryotic or prokaryotic system;
(v) blocking with heparin during selection, in a prokaryotic or eukaryotic system, especially when using yeast t-RNA;
(vi) encapsidating sbp member/ribosome complexes in a viral coat, e.g. TMV coat, in a prokaryotic or eukaryotic system;
(vii) encapsidating sbp member/ribosome complexes in a viral coat, e.g. TMV coat, in combination with incorporation of an MDV RNA template, in a prokaryotic or eukaryotic system
(viii) employing a mutagenic primer in RT-PCR generation of a DNA copy of the ribosome display library prior to a further round of selection, in a eukaryotic or prokaryotic system.

Any one or more of features (i) to (viii) may be employed in different aspects and embodiments of the present invention.

A method according to the present invention may be a method of obtaining a member of a specific binding pair (sbp) that binds a complementary sbp member of interest, the method comprising:

(a) providing mRNA molecules, each mRNA molecule comprising a nucleotide sequence encoding a specific binding pair member and lacking an in-frame stop codon;
(b) incubating the mRNA molecules under conditions for ribosome translation of the mRNA to produce the encoded specific binding pair member, whereby complexes each comprising ribosome, mRNA and encoded specific binding pair member displayed on the ribosome are formed;
(c) bringing the complexes into contact with the complementary sbp member of interest, and selecting one or more complexes displaying specific binding pair member able to bind the complementary sbp member of interest under the conditions of the selection.

RNA from a selected complex or complexes may be isolated and/or used in provision of DNA, which DNA may be used in production of the encoded specific binding pair member and/or employed in a further round of selection using ribosome display (or less preferably in this context bacteriophage display).

Generally a library, population or repertoire of diverse mRNA sequences is provided, encoding a library, population or repertoire of diverse peptides or polypeptides with the potential to form specific binding members.

The ribosome translation system employed may be prokaryotic or eukaryotic. Both have been successfully used in the art for display and selection of a number of different binding molecules. See for example: Mattheakis et al., (1994) PNAS USA 91, 9022–9026; Mattheakis et al., (1996) Methods Enzymol 267, 195–207; Gersuk et al., (1997) Biotech and Biophys Res Com 232, 578–582; Hanes and Pluckthun (1997) PNAS USA 94, 4937–4942; Hanes et al., (1998) PNAS USA 95, 14130–50; He and Taussig (1997) NAR 5132–5234.

A construct for ribosome display may comprise a RNA polymerase promoter (e.g. T7 polymerase promoter), ribosome binding site, Kozak consensus sequence, initiation codon and coding sequence of polypeptide, peptide or protein. One or more nucleotide sequences encoding one or more detection tags may be included to provide for production of a polypeptide, peptide or protein further comprising one or more detection tags (e.g. histidine tag). One or more features providing a feature according to the present invention or any combination thereof may be incorporated into a construct according to the present invention as disclosed herein.

A DNA construct may be cloned into any suitable plasmid or vector, e.g. pUC.

In accordance with one aspect of the invention, a method as outlined above is provided in which any one or more of features (i) to (viii) above is included (alone or in combination of any two or more, e.g. 3, 4, 5 , 6, 7 or 8).

Thus, in one aspect the present invention provides a method comprising steps (a), (b) and (c) as indicated, wherein each mRNA molecule comprising a nucleotide sequence encoding a specific binding pair member and lacking an in-frame stop codon further comprises sequence encoding a gly-ser tether to provide a fusion of encoded specific binding pair member and tether displayed on the ribosome surface. The tether may be provided C-terminally to the encoded specific binding pair member. A preferred poly-gly-ser tether for use in accordance with the present invention may comprise or consist of about 24 glycine-serine (GS) units, 10–50 GS units, 10–20, 10–30, 20–30, 20–40, 22, 23, 24, 25, 25 or 27 GS repeats. Other preferred tethers comprise 1–12 glycine-serine units. The tether may include one or more additional amino acids or tags at either end or both ends.

Experimental examples included below demonstrate that a gly-ser tether can be used in ribosome display. The number of specific antibodies generated by incorporation of a GS tether may be greater than in experiments that are identical except in use of a gene III based tether instead.

In a related aspect, the present invention provides a nucleic acid construct (DNA or RNA) for ribosome display comprising a nucleotide sequence encoding a glycine-serine (usually poly-glycine-serine) tether. Such a construct generally comprises additional features for ribosome display.

In embodiments of the present invention employing other aspects where a glycine-serine tether is not employed, a standard tether may be employed, e.g. using a domain of gene III of a filamentous bacteriophage (Hanes and Pluckthun, PNAS USA 1997, 94:4937–4942) or a kappa light chain constant domain (He et al, Febs Letts, 1997, 450: 105).

In another aspect the present invention provides a method comprising steps (a), (b) and (c) as indicated, wherein the translation system is eukaryotic and protein disulphide isomerase (PDI) is employed in the incubation conditions. PDI is available from Sigma and Pierce.

Experimental examples included below, demonstrate that use of PDI increases the amount of correctly folded specific binding member available to bind its cognate complementary binding molecule, and that the conditions when included in a modified ribosome display selection successfully generate antigen-specific antibodies.

In another aspect the present invention provides a method comprising steps (a), (b) and (c) as indicated, wherein protein disulphide isomerase (PDI) is employed in the incubation conditions, along with oxidised and reduced glutathione at a ratio of 1:1 and 10:1, in a eukaryotic or prokaryotic system.

In another aspect the present invention provides a method comprising steps (a), (b) and (c) as indicated, wherein oxidised and reduced glutathione is added after completion of initial translation, preferably about or after 30 minutes after translation initiation. This the inventors have found provides an improvement over addition at intitiation of translation.

In another aspect, the present invention provides a method comprising steps (a), (b) and (c) as indicated and further comprising selecting for complexes comprising a specific binding member able to bind complementary specific binding member of interest, while blocking unspecific selection using heparin. Example 7 below shows that including heparin as a blocking agent, especially in conjunction with use of yeast t-RNA, results in an improved level of recovered RNA.

In another aspect, the present invention provides a method comprising steps (a), (b) and (c) as indicated, wherein the mRNA further comprises a sequence for encapsidation of the mRNA in a viral coat. On provision of viral coat protein that recognises the sequence for encapsidation, the complex of mRNA, ribosome and displayed specific binding member is encapsidated in the viral coat protein.

The viral coat protein and OAS may be TMV (Durham (1972) J. Mol. Biol. 67, 289–305; Goelet et al., (1982) PNAS USA 79, 5818–5822). Other viral coat proteins such as those from the following virus families: Tobamovirus, Potexvirus, Potyvirus, Tobravirus, Cucumovirus or Comovirus, Togaviridae, Flaviviridae, Picornaviridae and Caliviridae along with their cognate packaging sequences may be used. Coat proteins derived from DNA viruses such as cauliflower mosaic virus may also be employed for encapsidating DNA or RNA, as can coat proteins of bacteriophages.

The viral coat protein may be provided prior to translation or co-translationally.

Incorporation of the OAS into the ribosome display construct allows the viral coat protein to nucleate encapsidation of the RNA construct. Coat protein is provided in a form suitable to initiate encapsidation. This form is preferably a "disc" preparation, as described in Durham (1972) J. Mol. Biol. 67, 289–305. It has been demonstrated in examples described below that an OAS can be inserted into the ribosome display construct and that RNA derived from this construct can be encapsidated in TMV coat protein. The encapsidated transcript can be translated in vitro to generate scFv of the appropriate size, hence packaged RNA retains the ability to be translated. Encapsidation of a single species of foreign (i.e. non TMV) RNA has been demonstrated by Sleat et al., (1986) Virology 166, 209–308, although encapsidation of populations of RNA has not been reported in the literature. It has been demonstrated that TMV is translated by a process of co-translational uncoating in which the plant ribosome simultaneously strips off the viral coat protein whilst translating the viral genome (Wilson (1985) J. Gen. Virol. 66, 1201–1207). This process of co-translational uncoating has also been shown for "pseudovirus" particles of foreign RNA produced in plants (Plaskitt et al., (1998) Plant-Microbe Interactions 1, 10–16), and is the likely mechanism of translation of the encapsidated ribosome display constructs. The presence of a ribosome on the OAS-containing RNA does not necessarily inhibit encapsidation of that RNA. It has been shown in an *E. coli* TMV coat protein expression system that encapsidation of the RNA can occur up to the position of the ribosome, at which point assembly is blocked (Hwang et al., (1994) PNAS USA 91, 9067–71).

Example 4 demonstrates successful packaging of mRNA/ribosome complex. Further addition of viral coat protein following translation may be used to repackage mRNA/ribosome/polypeptide complex to provide further stability.

In a related aspect, the present invention provides a nucleic acid construct (DNA or RNA) comprising the following elements RNA polymerase binding site, Kozak consensus sequence, ribosome binding site, initiation codon, coding sequence, tether sequence and OAS. One or more additionally features may be included.

In a further aspect the present invention provides a library or population of RNA molecules, each RNA molecule in the library or population containing a viral OAS and a sequence encoding a polypeptide or peptide specific binding member such as an antibody molecule, wherein the library or population collectively encodes a population or repertoire of specific binding members of diverse sequence. In preferred embodiments one or more additional features for ribosome display is included in the RNA molecules.

A library or population of RNA molecules according to the present invention may be packaged within viral coat, so a still further aspect of the present invention provides a population of viral particles, collectively harbouring or containing a population of RNA molecules encoding a population or repertoire of specific binding members of diverse sequence. Each viral particle in the population may contain RNA encoding a polypeptide or peptide of different sequence.

In addition to an origin of assembly sequence for viral coat protein, the mRNA molecules employed in a method comprising steps (a), (b) and (c) above may further comprise an MDV sequence for amplification by Qβ replicase. This enables replication of selected RNA populations without any necessity for a separate RT-PCR step.

In a related aspect, the present invention provides a nucleic acid construct (DNA or RNA) as disclosed and comprising an MDV sequence.

In a further aspect of the invention, mRNA molecules for incubation in the translation system are provided by means of RT-PCR reactions in which at least one of the RT-PCR primers is a mutagenic primer encoding a diversity of different sequences for inclusion in a defined region of the mRNA coding region, e.g. a region encoding a CDR of an antibody molecule, preferably CDR3 of an antibody VH domain.

Figure 7:
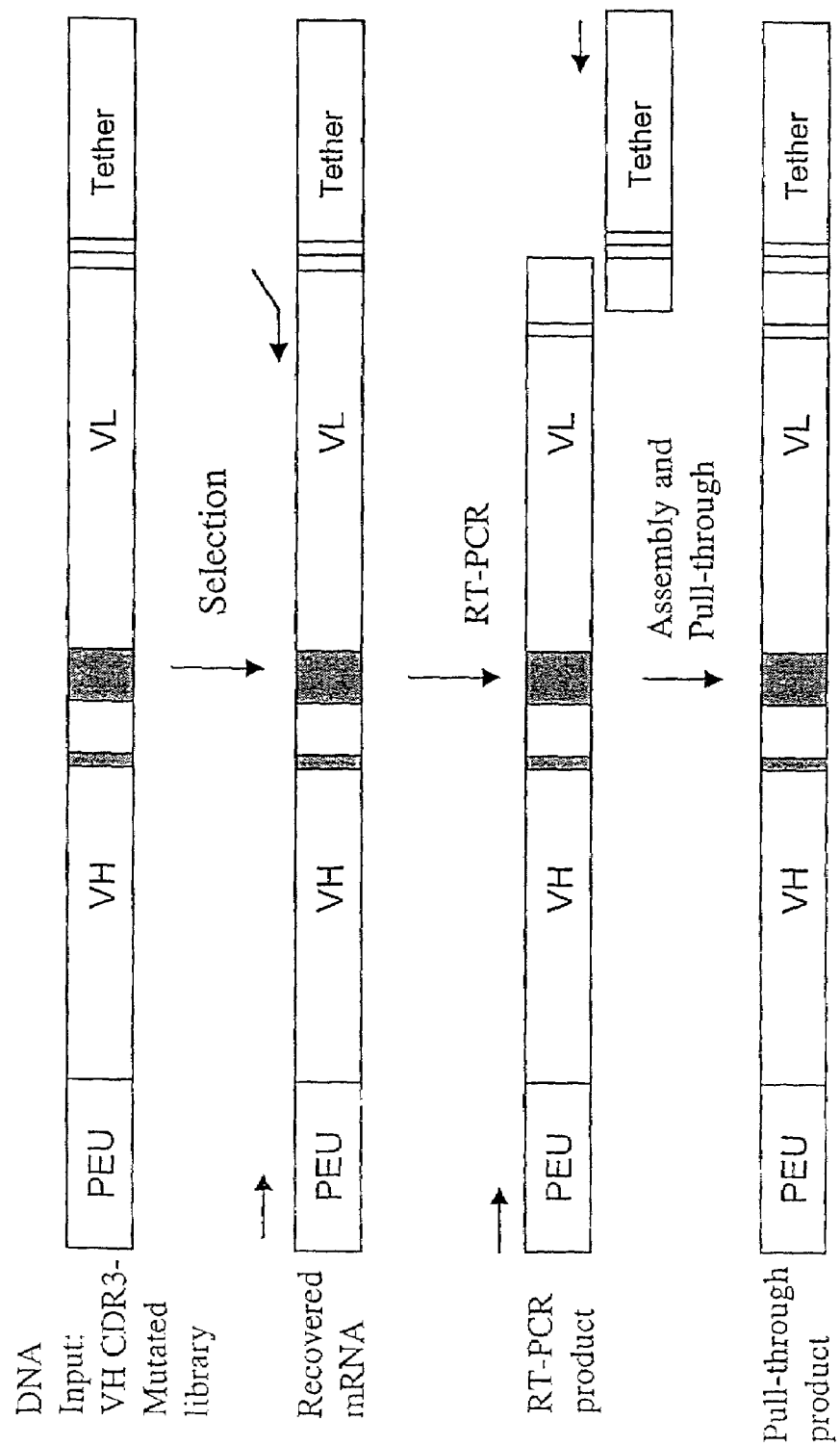
FIG. 7 illustrates a scheme in accordance with an embodiment of the present invention for targeted mutagenesis of a CDR of an antibody molecule VL domain, integrated into a ribosome display selection cycle.
Figure 8:
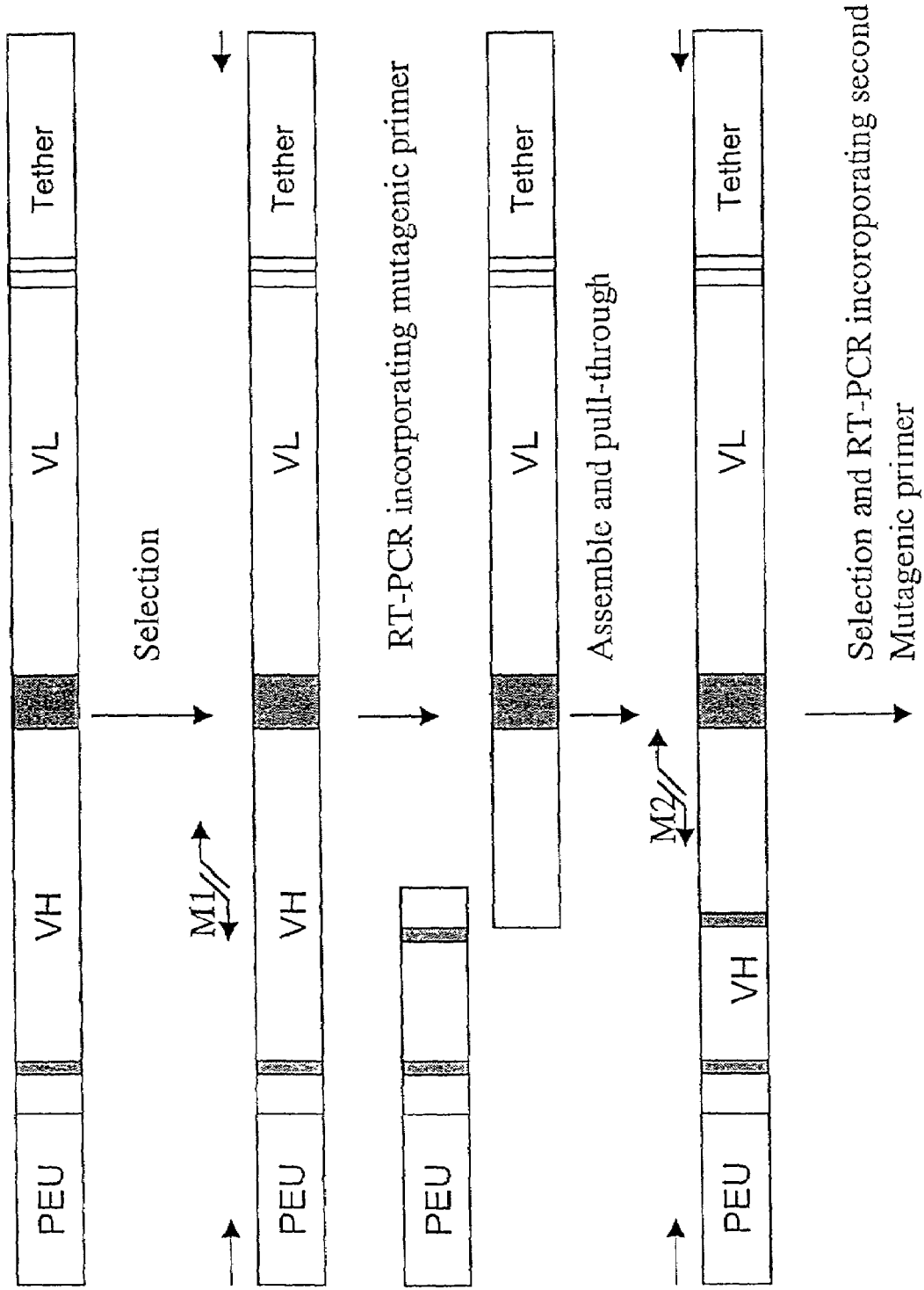
FIG. 8 illustrates a scheme in accordance with an embodiment of the present invention continuing on from the scheme illustrated in FIG. 7 and showing targeted mutagenesis of additional CDR=s, integrated into a ribosome display selection cycle.
Figure 9:
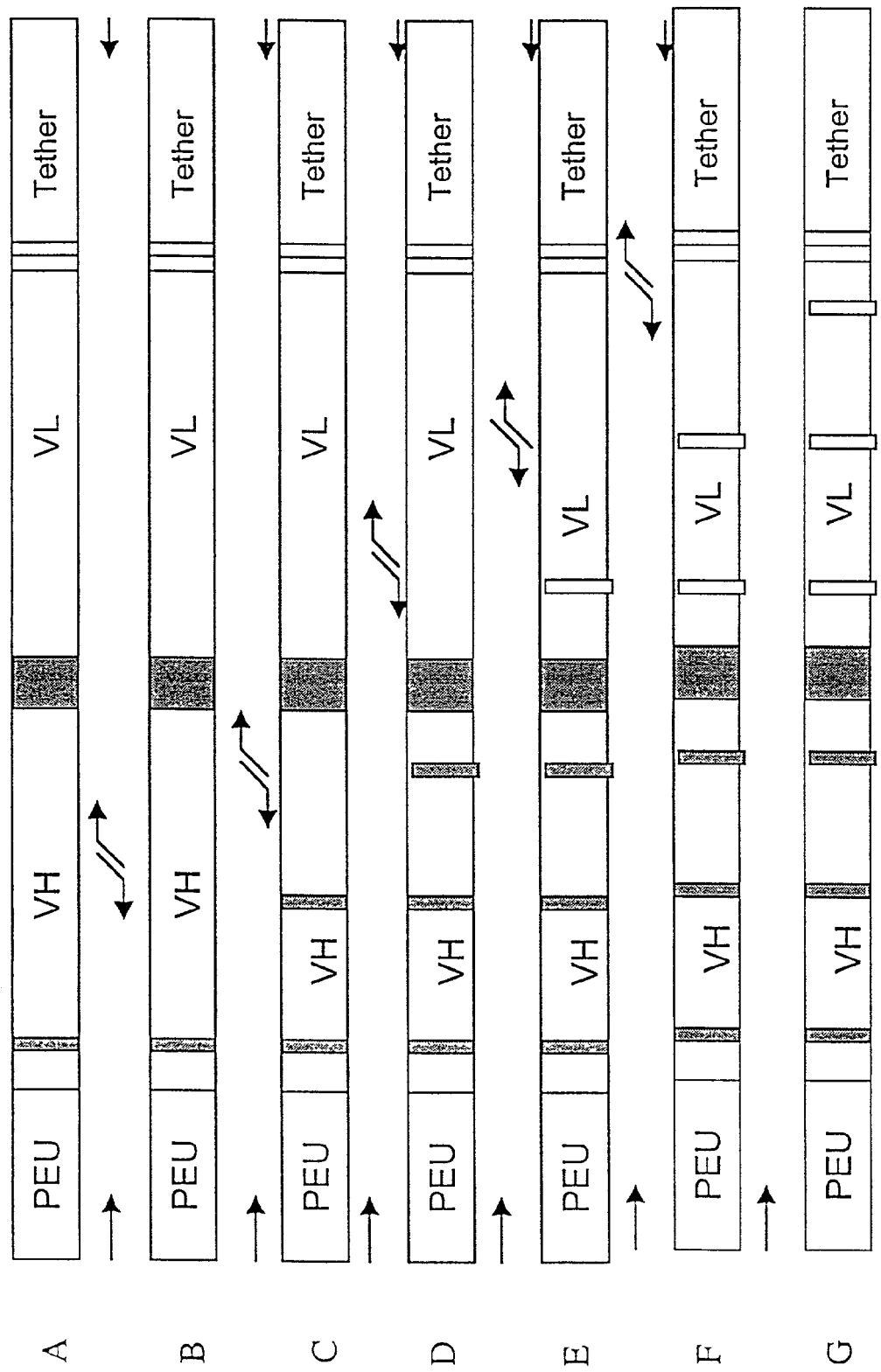
FIG. 9 illustrates a scheme in accordance with an embodiment of the present invention for successive mutagenesis of CDR=s of an antibody molecule in a ribosome display selection cycle.

Embodiments of this aspect of the invention are illustrated further in Examples 7 and 8, and in FIGS. 7, 8 and 9.

Further aspects of the present invention provide a library, population or repertoire of DNA or RNA molecules with the features disclosed for aspects concerned with nucleic acid constructs, wherein the library, population or repertoire of DNA or RNA molecules comprise the disclosed features for each of these aspects and collectively encode a diverse population of different polypeptides or peptides that may form specific binding pair members.

Still further aspects provide an expression system, such as an in vitro expression system, e.g. rabbit reticulocyte lysate or a bacterial system, comprising a nucleic acid construct or library, population or repertoire thereof, especially under culture conditions for translation of encoded polypeptide or peptide from the encoding nucleic acid.

In preferred embodiments, the specific binding members for display on the ribosomes are antibody molecules, usually single chain antibody molecules, such as scFv antibody molecules, VH, Fd (consisting of the VH and CH1 domains), or dAb molecules. Non-antibody specific binding members for display in other embodiments of the present invention include receptors, enzymes, peptides and protein ligands.

Following selection and retrieval of nucleic acid encoding the displayed specific binding member, the nucleic acid may be used in provision of the encoded specific binding member or may be used in provision of further nucleic acid (e.g. by means of an amplification reaction such as PCR). Nucleic acid encoding component parts of the specific binding pair member may be used in provision of further specific binding molecules, for instance reformatted antibody molecules. Thus, for example, nucleic acid encoding the VH and VL domains of a selected scFv antibody molecule may be used in construction of sequences encoding antibody molecules of other formats such as Fab molecules or whole antibody.

Furthermore, nucleic acid may be subject to any technique available in the art for alteration or mutation of its sequence. This may be used to provide a derivative sequence. A sequence may be provided which encodes a derivative of the selected specific binding member or component thereof, for example a derivative that comprises an amino acid sequence that differs from the selected specific binding member or component thereof by addition, deletion, insertion and/or substitution of one or more amino acid sequences. A method providing such a derivative may provide a fusion protein or conjugate wherein an additional peptide or polypeptide moiety is joined to the specific binding member or component thereof, e.g. a toxin or label.

Encoding nucleic acid, whether reformatted or not, may be used in production of the encoded polypeptide or peptide using any technique available in the art for provision of polypeptides and peptides by recombinant expression.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is *E. coli*.

The expression of antibodies and antibody fragments in prokaryotic cells such as *E. coli* is well established in the art. For a review, see for example Plückthun, A. Bio/Technology 9: 545–551 (1991). Expression in eukaryotic cells in culture is also available to those skilled in the art as an option for production of a specific binding member, see for recent reviews, for example Ref, M. E. (1993) Curr. Opinion Biotech. 4: 573–576; Trill J. J. et al. (1995) Curr. Opinion Biotech 6: 553–560.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology*, Second Edition, Ausubel et al. eds., John Wiley & Sons, 1992. The disclosures of Sambrook et al. and Ausubel et al. are incorporated herein by reference.

Thus, nucleic acid encoding a specific binding member selected using a method of the invention, or a component of such a specific binding member (e.g. VH and/or VL domain) may be provided in an expression system for production of a product polypeptide. This may comprise introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage.

The introduction may be followed by causing or allowing expression from the nucleic acid, e.g. by culturing host cells under conditions for production of the encoded product. The present invention also provides a method which comprises using a construct as stated above in an expression system in order to express a specific binding member or polypeptide as above.

Following production by expression, a product may be isolated and/or purified and may be formulated into a composition comprising at least one additional component. Such a composition may comprise a pharmaceutically acceptable excipient, vehicle or carrier.

Further aspects and embodiments of the present invention will be apparent to those skilled in the art in the light of the present disclosure. It should further be noted that all documents mentioned anywhere herein are incorporated by reference.

The present invention will now be further illustrated with reference to the following experimental examples.

List of Examples
Example 1—Monosome formation
Example 2—Improving ScFv refolding conditions for the ribosome display system
Example 3—Generation of a naïve PCR assembled library using a tether cassette
Example 4—Generation of a packagable PCR assembled library
Example 5—Generation of a packagable library which incorporates an RNA replicase cassette
Example 6—Generation of an affinity maturation library by PCR assembly
Example 7—An improved selection regime
Example 8—Use of the improved selection regime to select for affinity matured variants of an antibody isolated against a GPI-linked cell surface receptor.
Example 9—Comparison of structured versus unstructured tethers in a selection format

EXAMPLE 1

Monosome Formation a) Introduction

Efficient ribosome display selection will probably occur if one ribosome translates each mRNA molecule of the library, producing a single full-length protein molecule. If more than one ribosome translates a single mRNA molecule the additional ribosomes will be prevented from completely translating the mRNA due to the presence of the stalled, unreleased initial ribosome. The resultant translated protein molecules will be truncated and unable to assume correctly folded configurations. This may result in non-specific association of incorrectly folded material to the antigen in the selection process and may reduce its efficiency. The inventors anticipated that a 1:1 ratio of ribosome molecules to mRNA molecules may provide the most favourable circumstance to ensure the maximal library size is translated with only one ribosome per mRNA molecule.

b) Determination of the Number of Ribosomes per mRNA by Electron Microscopy

Nucleic acid with a sequence encoding a scFv antibody known to bind to FITC was cloned into a ribosome display vector (FIG. 2A, 2B—the construct cloned into a pUC-based vector) either with or without a terminal stop codon. The scFv coding region was then PCR amplified using primers PEU and HA mini to generate DNA fragments encoding the antibody downstream of the T7 promoter, ribosome binding site and Kozak consensus sequence. These PCR products (with or without a terminal stop codon) were then used as starting templates in a coupled rabbit reticulocyte transcription translation system with biotinylated lysine included in the translation mix to generate biotinylated scFv. Translation reactions were set up by making a master mix of 100 µl Promega rabbit reticulocyte lysate, 2.5 µl 1 mM methionine, 2 µl Promega Transcend tRNA and 15.5 µl sterile distilled water. 2 µl of PCR product (approximately 200 ng) was then added to 48 _l of the master mix and the reaction incubated for 1 hour at 30° C. Dilutions of the translation reaction were then immobilised on an electron microscope grid and stained with uyranyl acetate, followed by streptavidin-gold particles to label the biotinylated lysine residues.

In the case of the PCR fragment that included a stop codon at the end of the scFv gene no association of streptavidin gold with assembled ribosomes was observed. This is as expected, since the stop codon would allow release of the ribosome and hence dissociation of the antibody ribosome mRNA (ARM) complex. In the case of the PCR product that did not contain a stop codon the ARM complex remained intact, since the ribosome was not released. In this case the presence of streptavidin-gold particles in association with the assembled ribosomes was observed. The assembled ribosomes were observed in isolation, rather than in groups or lines. This is compelling evidence that monosomes rather than polysomes were generated by the translation process using the ribosome concentration and DNA template concentrations employed in the experiment.

EXAMPLE 2

Figure 2A:
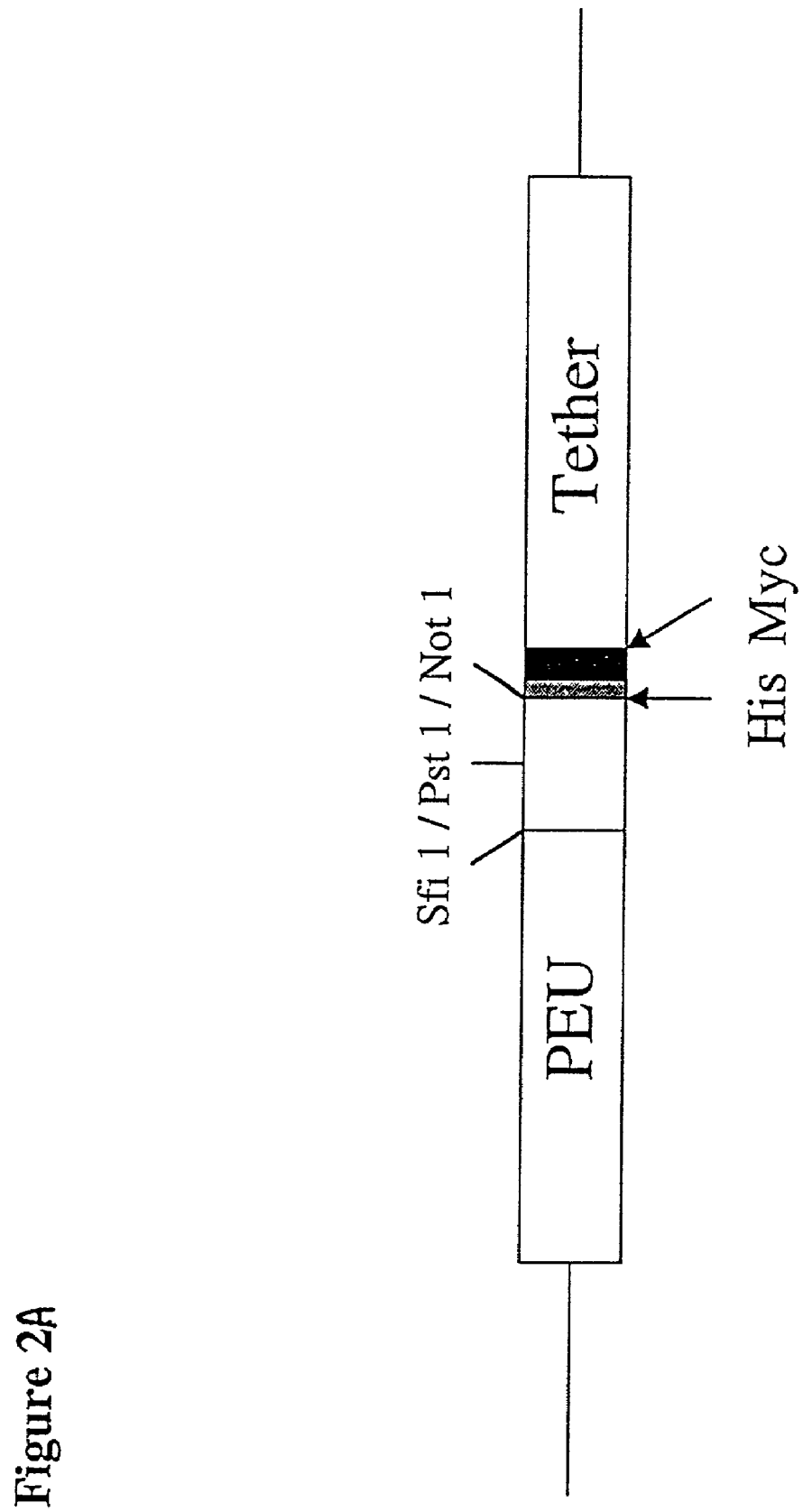
FIG. 2A illustrates key features: the protein expression unit (PEU) consists of T7 promoter, Kozak consensus sequence, ribosome binding site. Various cloning sites are included, as illustrated, and a sequence encoding a tether.
Figure 3:
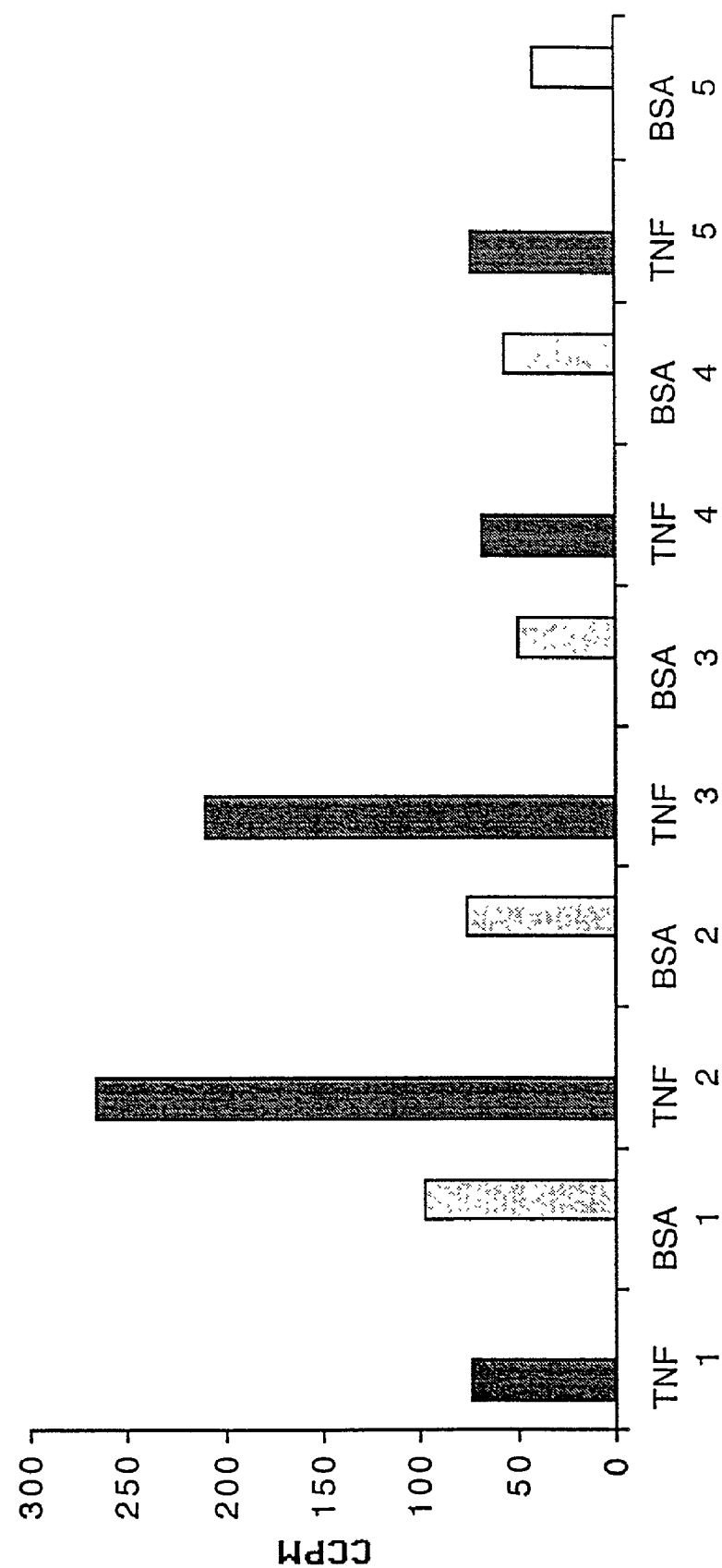
FIG. 3 shows the effect of redox state on activity of an antibody molecule (anti-TNFα scFv). A range of different ratios of oxidised:reduced glutathione was added to coupled reactions of an anti-TNFα scFv and tested on TNFα or BSA as a control. 1=buffer only; 2=10:1 oxidised:reduced; 3=1:1 oxidised:reduced; 4=1:10 oxidised:reduced; 5=reduced only.
Figure 4:
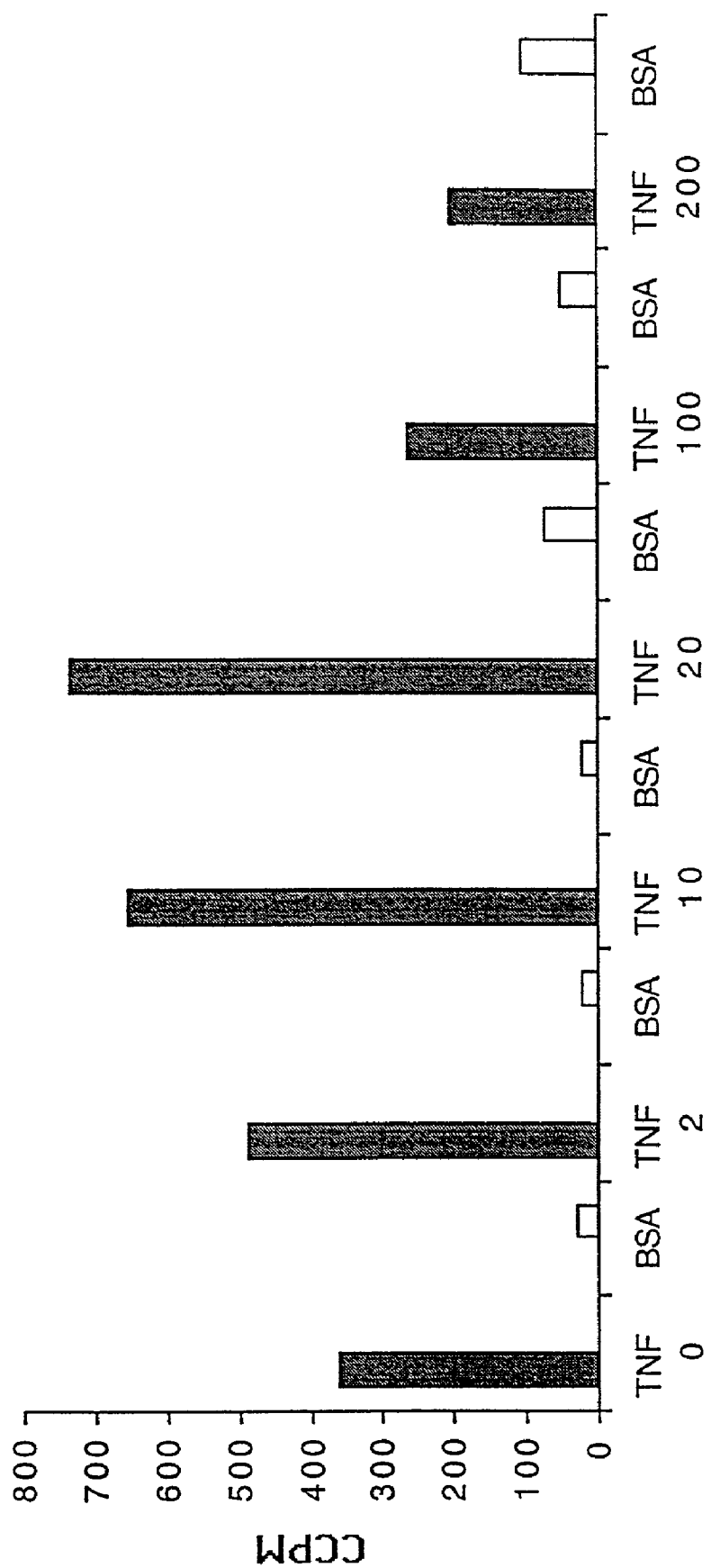
FIG. 4 ilustrates the effect of PDI concentraion on anti-TNFα scFv activity. Coupled reactions were performed with the antibody on TNFα or BSA as a control, at various titration concentrations of PDI (μg/ml).
Figure 5:
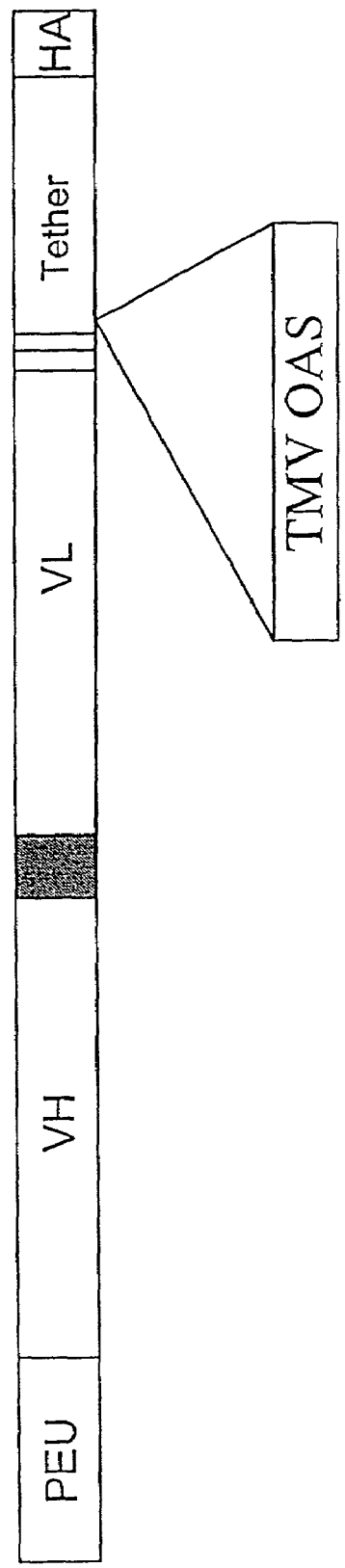
FIG. 5 illustrates a ribosome display construct with the addition of TMV OAS (origin of assembly sequence) for packaging, in accordance with an embodiment of the present invention.

Improving ScFv Refolding Conditions for the Ribosome Display System a) Introduction Much of the initial work on polysome display was carried out using peptide libraries in which protein folding conditions are not critical. The expression of larger protein or polypeptide libraries, such as antibody fragments, is potentially more dependent on the oxidation/reduction environment in which the protein is translated. The protein is folded as it is synthesised in eukaryotic systems and variation of the ratio of oxidised to reduced glutathione can significantly effect the efficiency of the folding process. Chaperones and protein disulphide isomerase (PDI) are more likely to be effective in prokaryotic systems because the newly synthesised protein is released from the ribosome prior to folding. In contrast, eukaryotic systems contain endogenous PDI (Ryabova et al, 1997, Nature Biotechnology, 15: 79–84) and no benefit to adding PDI to such a system could be expected. The present inventors have however shown that use of PDI, and use of PDI in combination with ox:red glutathione results in improved levels of recovered correctly folded specific binding members.

b) Effect of Variation in the Redox Potential of the In Vitro Translation Reaction on scFv Activity An assessment of the proportion of correctly folded scFv antibody fragments was made by subcloning a panel of existing scFv gene fragments that had been isolated by phage display (Table 1) into the ribosome display vector (FIG. 2A, 2B). These antibodies were then in vitro transcribed and translated using a coupled rabbit reticulocyte translation mix. $^{35}$S-methionine was included in the translation mix and production of active antibody was assayed by binding of the radiolabelled scFv to antigen. In vitro translations were set up by making a master mix of 100 µl TNT lysate, 2.5 μl 35S-methionine and 17.5 μl sterile distilled water. 2 μl of PCR product was then added to 48 μl of master mix and the reaction incubated for 60 min at 30° C. On completion of the reaction samples were treated with an equal volume (50 μl) of RNase and incubate at room temperature for 15 min. The samples were then blocked with 20μl of 18% Marvel in 6× PBS for 10 min. ELISA plates were coated with the appropriate antigen at 1 μg/ml at 4° C. overnight, then blocked for 1 hour at 37° C. with 200 μl of 3% Marvel in PBS. Half the blocked translation reaction was added to the antigen-coated wells and half to a well coated with a control protein, and allowed to bind for 1 hour at 37° C. After the incubation the liquid was removed using a pipette and the wells washed with 200 μl PBS containing 0.1% Tween, followed by three washes with 200 μl PBS. Bound scFv was eluted by adding 50 μl of 100 mM triethylamine (TES) to each well, and transferring this to a separate scintillation plate containing 25 μl of 1M Tris (pH 7.4) to neutralise the TEA. 100 μl of scintillation fluid was then added and the sample read on Top Count. Using the standard in vitro translation conditions of the commercially available translation kit 4/12 of the antibodies expression gave a detectable signal in the binding assay. The ratio of oxidised:reduced glutathione present in the translation mix was then varied and the panel of scFv antibodies tested in the binding assay under the new conditions. Ratios of: 10:1 oxidised:reduced; 1:1 oxidised:reduced; 1:10 oxidised:reduced and reduced only were included in the in vitro translation mix and were added after the reaction has proceeded for 30 min. A 1:1 ratio of oxidised reduced glutathione involved adding 50 μl of 4 mM oxidised glutathione and 4mM reduced glutathione. A typical example of the effect is shown in FIG. 3. At oxidised:reduced glutathione ratios of 10:1 and 1:1 the percentage of radioactivity labelled anti-TNF antibody which bound to the antigen was significantly increased. This trend of increase in active scFv at the 10:1 and 1:1 ratios held for all antibodies tested.

c) Assessment of the Effect of Addition of the Chaperone Protein Disulphide Isomerase on scFv Activity The panel of scFv antibodies cloned into the ribosome display vector were assessed for binding to antigen in ELISA format by the capture of radiolabelled antibody. Translation mixes were set up as described above. An oxidised:reduced glutathione ratio of 1:1 was included in the translation mix and protein disulphide isomerase (PDI) was added at a range of concentrations from 0 to 200 μg/ml. It was found that PDI added at a concentration of 10–20 μg/ml enhanced the signal obtained in the capture assay. Example results showing the effect of PDI on scFv activity appear in FIG. 4.

The time of addition of PDI to the translation mix was also assessed. PDI was added at 0, 10, 20 or 30 minutes after the start of the translation reaction, and little change in captured scFv was observed, suggesting the time of addition is not critical.

d) Summary of Improved scFv Folding Conditions In Vitro Translation Reactions.

In vitro translation reactions for the production of greater amounts of correctly folded scFv have been determined to be the inclusion of about 20 μg/ml PDI at time zero in the reaction mix. After the reaction has proceeded for 30 mins 4 mM GSSG, and 4 mM GSH are added (1:1 oxidised : reduced glutathione) and the reaction is continued for a further 30 min. Reaction temperature is 30° C. Under these conditions the number of scFv which gave detectable binding in the capture assay increased from 4/12 under standard translation conditions to 7/12. These data are summarised in Table 2. The specificity of none of the scFv tested was altered by the modified translation conditions.

EXAMPLE 3

Generation of a Naïve PCR Assembled Library Using a Tether Cassette a) Introduction For an effective ribosome display repertoire to be produced a tether is included to provide a spacer between the ribosome and the displayed polypeptide.

Tethers used to date described in the literature have comprised fragments of naturally occurring structured proteins such as the gene III protein of the filamentous bacteriophage Fd (Hanes and Pluckthun, PNAS USA 1997, 94, 4937–4942) or antibody constant domains (He and Taussig, NAR, 1997, 25, 5132–5134). We have incorporated a synthetic glysine-serine tether into the ribosome display construct which will have little integral secondary structure, as compared to the tethers already described. This may be used to reduce the stringency of the folding conditions required for efficient ribosome display of a given protein and provide more flexibility in the tether region, reducing possible stearic hindrance effects between the ribosome and the expressed protein. The tether fragment may vary in length from 2 amino acids to about 400 amino acids, e.g. one glycine-serine unit to up to about 200 glycine-serine units, and may encode other peptides or proteins which have limited secondary structure. It is also possible to use the tether cassette as a way of incorporating other types of encoded function into the the ribosome display repertoire. For example sequences encoding packaging signals, or RNA replicase sequences may also be included.

b) Generation of PCR Assembled Library

A scFv antibody repertoire was PCR amplified from an expanded version of the phage display scFv library cloned into pCantab6 (Vaughan et al 1996). PCR was carried out using the primers PEU and mycseq10 using 30 cycles of 94° C. 1 min, 55° C. 1 min, 72° C. 2 min, and the resultant PCR product was gel purified. A tether fragment was produced by PCR of the RDV-stuffer vector (FIG. 2A, 2B) using primers hismyc Back and HA tag using the same PCR conditions as the scFv. Assembly and pull through reactions were carried out using the primers T7 and HA mini (Appendix II). Assemblies were carried out using 25 cycles of 94° C. 1 min, 55° C. 4 min. One tenth of the assembly reaction (5 μl) was then added to a pull through reaction and PCR amplified using 30 cycles of 94° C. 1 min, 55° C. 1 min, 72° C. 2 min. The pull through reaction is a PCR that uses primers which are at the extreme ends of the two DNA fragments being annealed in the assembly reaction. In this way, full length assembled product is amplified from the fragment mixture. An assembled product of the expected size (1.1 kb) was produced and gel purified. This product can be used directly as starting template for a coupled in vitro translation/transcription reaction. Primers used (all written 5'-3'):

```
PEU (SEQ ID NO: 2)
AA TTC TAA TAC GAC TCA CTA TAG GGA GAG CAC TTC TGA

TCC AGT CCG ACT GAG AAG GAA GGC CCA GCC GGC CAT GG
```

-continued

HA TAG (SEQ ID NO: 3)
TAC CCG TAT GAC GTG CCG GAT TAC GCA

T7 (SEQ ID NO: 4)
TAA TAC GAC TCA CTA TAG GGA GAG CAC TTC TG

HA mini (SEQ ID NO: 5)
TGC GTA ATC CGG CAC

Mycseq 10 (SEQ ID NO: 6)
CTC TTC TGA GAT GAG TTT TTG

Hismyc back (SEQ ID NO: 7)
GCA CAT CAT CAT CAC CAT CAC GGG GCC c) Characterisation of the PCR Assembled Library on the Basis of scFv Exoression The scFv repertoire assembled with a glycine-serine tether was used as template in an in vitro translation reaction using the conditions described in Example 7. The translation reaction was run out on a protein gel and western blotted. ScFv was detected by probing the blot with an anti-myc tag antibody, followed by and anti-species HRP conjugate. Levels of scFv production from the assembled library were estimated to be between 50–100 μg/ml.

d) Analysis of Sequence Diversity of the Unselected PCR Assembled Library

A fraction of the library was digested with the restriction enzyme Bst Ni which has a frequently occurring four residue recognition sequence. On digestion of the library with this enzyme a ladder of bands resulted, demonstrating that the library consists of a mixed population of scFv gene segments. When the library was digested with Sfi I a single band was observed of the expected size. A fraction of the library was also digested with Sfi I and Not I and cloned into the ribosome display vector to allow sequencing of individual scFv gene fragments present in the library. 48 scFv fragments were sequenced and all were found to different. These data provide indication that the population of scFv gene segments present in the PCR assembled library is diverse.

EXAMPLE 4

Generation of a Packagable PCR Assembled Library

Incorporation of TMV OAS into Constructs for Ribosome Display Libraries.

The core positions of the OAS correspond to positions 5420–5546 of the TMV RNA sequence (Goelet et al., 1982, PNAS USA 79, 5818).

A library of scFv fragments was generated by PCR amplification, as described (Example 3). Polyhistidine and myc tags were retained in the PCR fragments 3= to the scFv coding region. An origin of assembly-containing PCR fragment was generated by the ligation of two oligonucleotides as follows.

Oligonucleotides HA-OAS1 and HA-OAS2 were assembled together by the addition of 2 μl (approximately 100 ng) of each oligo to 24 μl 1×TAQ buffer containing 1.5 μl of 5 mM dNTPs and 0.5 μl TAQ polymerase. The assembly reaction conditions were 94° C. for 1 min, followed by 55° C. for 4 min in 6 cycles. A pull-through reaction was set up consisting of 10 μl of the assembly reaction added to 5 μl of scFv repertoire (approximately 500 ng which had been PCR amplified with PEU and mycseq, Example 3), 5 μl 5 μM dNTPs, 5 μl 10×PCR buffer, 2.5 μl of HAmini primer (10 μM), 2.5 μl PEU (10 μM), and 0.5 μl TAQ. PCR conditions were 25 cycles of 94° C. 1 min, 55° C. 1 min, 72° C. 2 min. After pull-through reactions were complete a band of approximately 1.1 kb corresponding to assembled scFv and OAS tether was visible after gel electrophoresis.

HA-OAS 1 (135mer) (5'-3') (SEQ ID NO: 8):
TGC GTA ATC CGG CAC GTC ATA CGG GTA ACT ATT TTT CCC TTT GCG

GAC ATC ACT CTT TTT TCC GGT TCG AGA TCG AAA CTT TGC AAG CCT

GAT CGA CAT AGG GAC ATC TTC CAT GAA CTC ATC AAC GAC TTC TTC

HA-OAS 2 (no stop) (144mer) (5'-3'): (SEQ ID NO: 9):
GAA CTC ATC AAC GAC TTC TTC TGT AAG TTC CAT GGG CCC TCC GTC

TCT CAC GTT TGT AAT CTT CTC TCT CAA ACC ATT CAG ATC CTC TTC

TGA GAT GAG TTT TTG TTC TGC GGC CCC GTG ATG GTG ATG ATG ATG

TCG GGC CGC

A version of primer OAS 2 was also produced which incorporated a stop codon at the end of the myc tag. This oligonucleotide allows production of OAS-containing constructs which will not have the ability to form ARMs complexes because the presence of the stop codon will result in release of the ribosome.

HA-OAS 2 stop (5'-3') (SEQ ID NO: 10):
GAA CTC ATC AAC GAC TTC TTC TGT AAG TTC CAT GGG CCC TCC GTC

TCT CAC GTT TGT AAT CTT CTC TCT CAA ACC CTA ATT CAG ATC CTC

TTC TGA GAT GAG TTT TTG TTC TGC GGC CCC GTG ATG GTG ATG ATG

ATG TCG GGC CGC c) RNA Transcription

RNA was generated by in vitro transcription of the PCR product. A transcription reaction was assembled by the addition of approximately 4 µg of PCR product (in 20 µl water) to 10 µl transcription buffer, 25 mM rNTPs, and 5 µl Promega T7 enzyme mix. The reaction was incubated for 2 hours at 37° C. On completion of the reaction Dnase I was added and the reaction incubated for 15 min at 37° C. The transcription reaction was then phenol/choloroform extracted and divided into 4 aliquots of 12.5 µl. 37.5 µl of water was added to each aliquot and the RNA then ethanol precipitated by the addition of 5 µl of 3M sodium acetate, 1 µl glycogen and 125 µl 100% ethanol. Precipitation was carried out at B70° C. for 30 min, and the RNA then pelleted by centrifugation at 13 000 rpm for 10 min in a microfuge. Pellets were washed in 70% ethanol and resuspended in 50 µl water. RNA was stored at B70° C.

d) Preparation of TMV Coat Protein

The method of preparation of TMV coat protein was based on that described by Durham, 1972 J Mol Biol 67 289–305. The method involves dialysis of TMV in a high pH buffer (pH11) to disaggregate the coat protein from the viral RNA. This is followed by dialysis at pH 8 and capture of the free RNA on a DEAE-cellulose column. The protein is then eluted from the column in a small volume and dialysed in pH 5 buffer to give a disc preparation of the coat protein.

0.5 ml of 10 mg/ml U1 strain TMV was dialysed overnight at 4° C. in 0.1M ethanolamine containing 0.005M HCl. Virus was dialysed for 4 hr against 0.012M Tris/0.01M HCl, and the degraded virus centrifuged at 150 000 g for 1 hr. The supernatant was loaded onto a 1 ml DEAE cellulose column which had been pre-equilibrated with 0.12M Tris/0.01M HCl, and the coat protein was eluted with 0.12M Tris/0.1 M HCl. 1 ml fractions were collected and the bulk of the protein was collected in fraction 2. The coat protein was then dialysed for a minimum of 48 hr at 4° C. in sodium acetate I=0.1, pH5.

e) Packaging Reactions.

Packaging reactions were carried out as described by Sleat et al, 1986 Virology 155, 299–308. A protein:RNA ratio (w/w) of 50:1 was chosen for the reactions. Primary packaging reactions were set up using 7 µg of transcribed RNA and 350 µg of coat protein preparation. Total reaction volume was 1 ml made up with 0.1 M TrisHCl pH 8, and incubation was for 2 hr at room temperature. After packaging was complete the reactions were stored at 4° C.

The success of the packaging reactions was assayed by electron microscopy. Samples from the original virus preparation, the coat protein preparation and the packaging reactions were viewed in the electron microscope after negative staining with 1% (w/v) uranyl acetate. The original virus and in vitro transcribed RNA packing reaction gave clearly visible rods, the in vitro packaged RNA generating shorter rods than the parental virus. No rods could be seen in the protein preparation.

This demonstrates encapsidating RNA to improve stability of the RNA during long term storage and during the selection process. Encapsidated RNA can be directly translated in vitro in a process called co-translational disassembly to allow generation of the ARM complex. Further viral coat protein may be added to the in vitro translation reaction after co-translational disassembly has occurred to allow repackaging of the polypeptide/ribosome complex with the polypeptide still displayed. This would generate a stable complex the RNA of which would be less prone to degradation than the unencapsidated RNA.

It is possible to express TMV coat protein in *E. coli* along with the OAS-containing RNA to generate in vivo packaged pseudovirus particles (Hwang et al., Proc. Natl. Acad. Sci. USA 91, 9067–9071). This may be used to provide a means to co-express TMV coat protein and mRNA encoding an OAS-containing scFv library to generate a packaged library in vivo.

EXAMPLE 5

Figure 6:
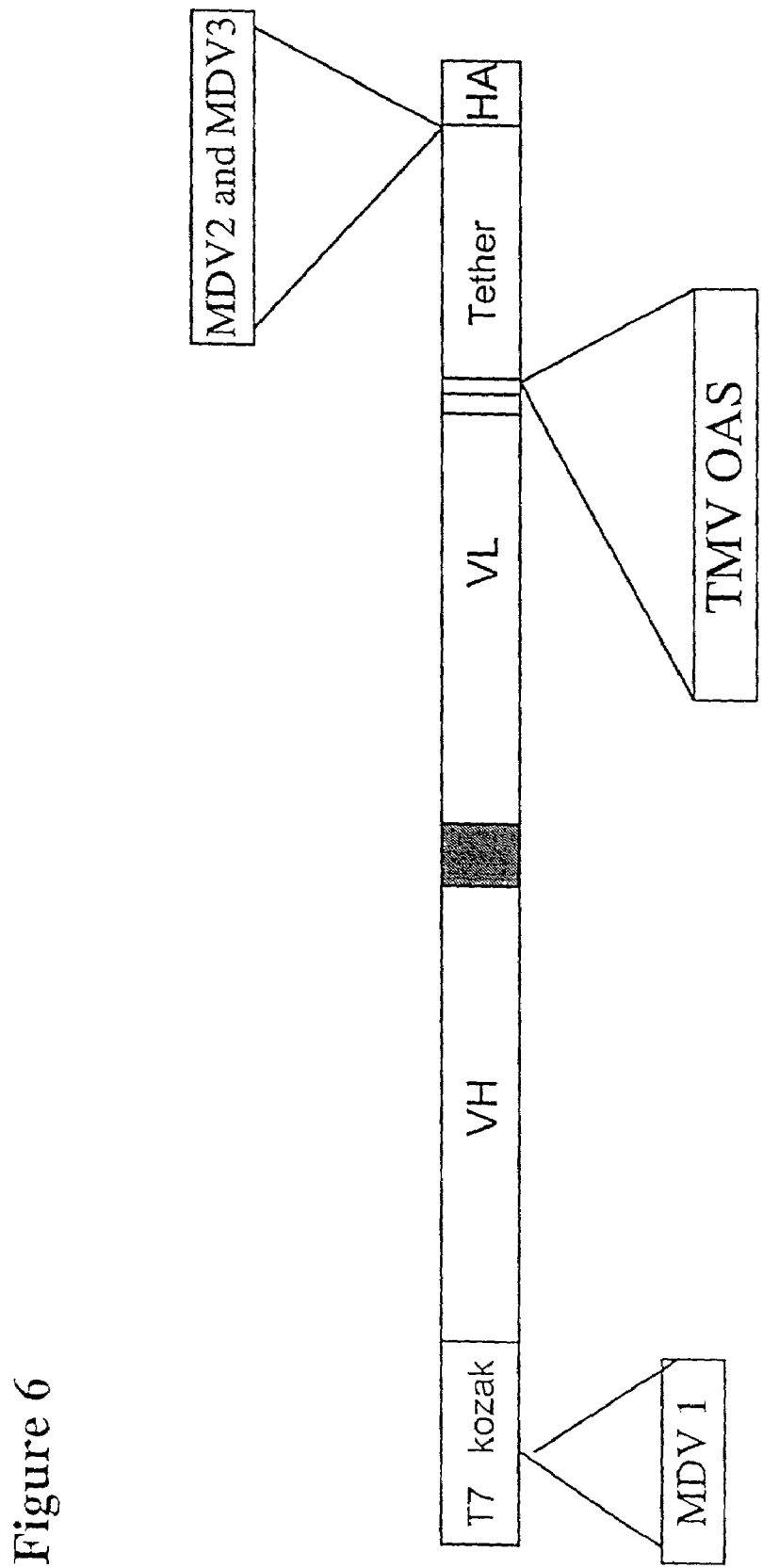
FIG. 6 illustrates a ribosome display construct with the addition of TMV OAS (origin of assembly sequence) for packaging, and MDV sequences as substrate for replicase, in accordance with an embodiment of the present invention.

Generation of a Packagable Library which Incorporates an RNA Replicase Cassette a) Design of Replication Sequence Cassette Midivariant (MDV) RNA is a template for the RNA-directed RNA polymerase Qβ replicase (Wu et al., Proc. Natl. Acad. Sci. 89, 1992 11769–73). The MDV RNA consists of two separate regions of RNA which hybridise together to form a distinct secondary structure which enables the Qβ replicase to recognise the RNA and catalyse its exponential amplification. The present inventors have included the sections of MDV RNA in a ribosome display construct that generates RNA that can be replicated in vitro. Such a construct may also include the TMV or other viral OAS packaging sequence to allow encapsidation of the resultant RNA molecules. The design of a ribosome display construct incorporating MDV and OAS sequences is shown in FIG. 6.

Primers to allow the incorporation of MDV RNA into the ribosome display construct are shown below:

The MVD1 replication site includes 63 nucleotides at the 5=end of the construct as follows (5'-3'): GGGGAC-CCCCCCGGAAGGGGGGGACGAGGT-GCGGGCACCTCGTACGGGAG TTCGACCGTGACG (SEQ ID NO: 11).

This 63 nucleotide segment is then followed by the expression unit containing the scFv gene segments, detection and purification tags, the TMV GAS sequence if required and a tether. The 3' end of the construct then includes the 3' MDV sequence that is 156 nucleotides long as follows (5"-3'): CACGGGCTAGCGCTTTCGCGCTCTC-CCAGGTGACGCCTCGTGAA GAGGCGCGACCT-TCGTGCGTTTCGGTGACGCACGAGAACCGCCACG CTGC AGCGTGGCTCCTTCGCGCAGCCCGCT-GCGCGAGGTGACCCCCCGAAGGGGGGTC CC (SEQ ID NO: 12).

The 3=segment of the MDV sequence is too long to be made as a continuous oligonucleotide, so is split into two overlapping segments which can be made as single oligonulcoetides which can be annealed together. Three MDV oligonucleotides in total are required as follows:

MVD1 (encoding the 5=63 nucleotides of the MDV sequence followed by 23 nucleotides of the T7 promoter shown in bold) (5'-3').

GGGGACCCCCCCGGAAGGGGGGGACGAG-GTGCGGGCACCTCGTACGGGAGTTC ACCGTGAC-GAATTCTAATACGACTCACTATAG (SEQ ID NO: 13)

MDV2: HA detection tag (bold face) followed by the first 79 nucleotides of the 3=segment of the MDV RNA.

Sense

TACCCGTATGACGTGCCGGATTACGCA-CACGGGCTAGCGCTTTCGCGCTCTCCC GTGACGC-CTCGTGAAGAGGCGCGACCTTCGT-GCGTTTCGGTGACGCACGA (SEQ ID NO: 14)

Reverse complement (5'-3')

TCGTGCGTCACCGAAACGCACGAAG-
GTCGCGCCTCTTCACGAGGCGTCACCTGG
AGAGCGCGAAAGCGCTAGCCCGTGTGCG-
TAATCCGGCACGTCATACGGGTA (SEQ ID NO: 15)

MVD3: Remaining 77 nucleotides of the 3' MDV segment within an additional 19 nucleotide overlap (bold face) with MDV2 to allow assembly.

Sense

GCGTTTCGGTGACGCACGAGAACCGC-
CACGCTGCTTCGCAGCGTGGCTCCTTCGCG CAGC-
CCGCTGCGCGAGGTGAC-
CCCCCGAAGGGGGGTTCCC (SEQ ID NO: 16)

Reverse complement

GGGAACCCCCCTTCGGGGGGTCAC-
CTCGCGCAGCGGGCTGCGCGAAGGAGCCACG
CTGCGAAGCAGCGTGGCGGTTCTCGT-
GCGTCACCGAAACGC (SEQ ID NO: 17) b) Assembly Conditions MVD2 and MVD3 oligonucleotides were assembled together by the addition of 2 µl of each oligo to 24 µl 1×TAQ buffer containing 1.5 µl of 5 mM dNTPs and 0.5 µl TAQ polymerase. The assembly reaction conditions were 94° C. for 1 min, followed by 55° C. for 4 min in 6 cycles. A three way pull-through reaction was set up consisting of 10 µl of the assembly reaction, 2 µl of MDV1 oligonucleotide and 5 µl of scFv OAS repertoire (approximately 500 ng which had been PCR amplified with PEU and HA back, Example 3), 5 µl 5_M dNTPs, 5 µl 10×PCR buffer, 2.5 µl of MDV3 (10_M), 2.5 µl PEU (10_M), and 0.5 µl TAQ. PCR conditions were 25 cycles of 94° C. 1 min, 55° C. 1 min, 72° C. 2 min. After pull-through reactions were complete a band of approximately 1.3 kb corresponding to the fully assembly product was gel purified. This DNA was then digested with Sfi I and Not I and cloned into Sfi I/Not I cut ribosome display vector, allowing transcription of the full length mRNA which could then be replicated with Qβ replicase, or packaged in TMV CP.

EXAMPLE 6

Generation of an Affinity Maturation Library by PCR Assembly

The PCR assembly strategy described in Example 3 is applied to generation of libraries designed for affinity maturation of a parental scFv. The PCR primers are designed to generate the main body of parental scFv from the first few residues of the VL CDR3 through to the start of the heavy chain, as shown in FIG. 7. The remaining portion of the VL CDR3 (the area to be targeted by the mutagenesis) is then generated using a mutagenesis primer which overlaps with the start of the VL CDR3 paired with a primer terminal to the tether (e.g. HA back) as shown in FIG. 7. The two fragments are assembled and pull through using standard conditions to provide template for a ribosome display selection. This procedure may be modified to generate libraries of mutants in each of the CDRs as shown in FIG. 8. It may also be used to sequentially mutate different CDRs at each round of selection, as shown in FIG. 9.

EXAMPLE 7

An Improved Selection Regime a) Introduction

A polypeptide which binds a complementary sbp member of interest (e.g. antibody molecule that binds antigen of interest) can be selected from a library of polypeptides displayed on ribosomes using the complementary sbp member (e.g. antigen) either coated onto panning tubes or in solution. Once the binding molecules are captured RNA is eluted and put into a reverse transcriptase BPCR (RT-PCR) to generate DNA. This DNA can then either be cloned into a ribosome display vector (or other expression vector) or can be re-assembled to include a protein expression unit and appropriate tether and can be subjected to further rounds of selection. This process is reliant on keeping the RNA molecule in association with the ribosome in the initial stage of the selection and ensuring that the eluted RNA is full length so that full length polypeptide-encoding DNA can be regenerated from it. An example of a protocol used to select anti-FITC antibodies from a naive library in accordance with various aspects of the present invention is described below.

b) Selection

A panning tube was coated with 1 ml of FITC-BSA at 100 µg/ml overnight at room temperature. The next day the tube was blocked with 2 ml 10% BSA containing 1 mg/ml tRNA and the tube was shaken for 1 hour at room temperature, and then for 1 hour at 4° C.

A master translation mix was prepared by the addition of 93.7 µl TNT lysate to 2.4 µl 1 mM methionine, 2.3 µl PDI (at 20 µg/ml) and a maximum volume of 26.6 µl PCR assembled library (1–2 µg). This mix was split into two reactions of 62.5 µl and incubated at 30° C. for 30 min, after which an equal volume of 4 mM 1:1 oxidised:reduced glutathione (GSSG:GSH) was added. The reaction was incubated for a further 30 min at 30° C. and diluted immediately into 750 µl ice-cold heparin at 2.5 mg/ml in 1×TBS containing 0.1% Tween, 5 mM MgOAc. Coated panning tubes were washed 3–5 times with 1 ml of the heparin block solution at 4° C. The translation reaction was then added to the tube and shaken gently for 1 hour at 4° C. All remaining steps were carried out at 4° C. using ice-cold tips and tubes. The tubes were washed 10 times with 2 ml heparin block and the RNA then eluted with 200 µl elution buffer (20 mM EDTA, 1×TBS, RNase inhibitor at 1 U/µl). To ensure efficient elution the tubes were vortexed several times over 10 min. 100 µl PBS was then added to the eluted sample, along with 400 µl lysis buffer from a Boehringer High Pure RNA Isolation kit. RNA was purified as described in the kit and eluted in 50 µl of kit elution buffer.

c) RT-PCR

RT-PCR was carried out using the purified RNA as template using an AB gene RT-PCR kit. A mix for one RT-PCR consisted of 25 µl enzyme mix, 1 µl RT-enzyme, 5 µl RNA, 1 µl Bigpam primer (10 µM), 1 µl Myc37 primer (10 µM), 17 µl water. Control reactions with no added RT enzyme were set up in parallel to demonstrate absence of DNA contamination. PCR conditions were 30 cycles of 94° C. 1 min, 64° C. 1 min, 72° C. 2 min. The resultant PCR product was either cloned as a Sfi I/Not I fragment into RDV or pCantab6, or was reassembled into a full-length ribosome display as described below.

d) Re-Assembly of RT-PCR Product 100 ng gel purified RT-PCR product and 50 ng tether PCR fragment were made up to 50 µl with water and 1 µl glycogen, 5 µl 3M sodium acetate and 150 µl 100% ethanol were added. The DNA was precipitated at B70° C. for 30 min, then pelleted in a minifuge at 13 000 rpm for 20 min at 4° C. The pellet was washed in 70% ethanol and resuspended in 25 µl water. The DNA was transferred to strips of 0.2 ml PCR tubes and 3 µl Taq buffer, 1.5 µl dNTPs and 0.51 µl TAQ then added. The assembly reaction was carried out using 25 cycles of 94° C. 1 min, 65° C. 4 min. 5 µl of the assembled product was added to a standard PCR mix containing the primers PEU1 and HA Back using an annealing temperature of 58° C. PCR products were gel purified and could then be used as input for a second round of selection.

e) Screening of Selection Outputs

To allow screening of outputs from the various rounds of selection RT-PCR products were disgested with Sfi I/Not I and cloned into the phage display vector pCantab6. Individual colonies resulting from this cloning could then be picked and screened for binding to target antigens by phage ELISA, as described in Vaughan et al., 1996.

f) Characterisation of an Anti-FITC Clone Selected from the Naïve PCR-assembled Ribosome Display Library Phage ELISA of a population of scFv generated by two rounds of selection of the PCR-assembled naive ribosome display library on FITC-BSA identified a FITC-specific scFv. The cloned had a DP50 VH germline, and DP116 VL germline. CDR3s were as follows:

| VH CDR3 | NMVRGVGRYYYMDV (SEQ ID NO: 18) |
| VL CDR3 | CSRDSSGYHLV (SEQ ID NO: 19) |

The off rate of this clone was measured by BiaCore and found to be $5 \times 10^{-3}$ $s_{-1}$.

EXAMPLE 8

Use of the Improved Selection Regime to Selection for Affinity Matured Variants of an Antibody Isolated Against a GPI-Linked Cell Surface Receptor a) Mutagenised Libraries A parental scFv that recognised the GPI-linked cell surface receptor of interest was isolated from a large phage display library using standard selection techniques. The parent clone had a $K_d$ of 0.02 $s^{-1}$, as measured by BiaCore analysis of FPLC purified monomeric scFv.

The VH CDR3 of the parent had the following sequence: VHNGWYALEY (SEQ ID NO: 20).

The VL CDR3 of the parent had the following sequence: NSWDSSGNHVV (SEQ ID NO: 21).

Libraries in which the central five residues of either the VH or VL CDR3 were mutated were generated by oligonucleotide mutagenesis and cloned into the ribosome display vector.

Libraries were designed as follows:

| Library H4 (VH CDR3) | VHNXXXXXEY (SEQ ID NO: 22) |
| Library L4 (VL CDR3) | NSWXXXXXHVV (SEQ ID NO: 23) | b) Selections

RNA was transcribed from plasmid prepared from each of the libraries using standard protocols. A typical transcription reaction was: 4 µl 5× transcription buffer (Promega); 20 units Rnasin; 4 µl of each ATP, GTP, UTP, CTP (2.5 mM); 1 µl T7 RNA polymerase; 100 ng plasmid DNA, made up to 20 µl with nuclease-free water. RNA from each library was used as input for the first round of selection, and subsequent selections were carried out using linear DNA as input as described in Example 7. The first two rounds were carried out using the target antigen immobilised onto plastic exactly as described in Example 7. This was performed for both the H4 and L4 libraries. Two further rounds of selection were carried out on the L4 library using biotinylated antigen at concentrations of 100 nM for round 3 and 10 nM for round 4. Selections using biotinylated antigen were carried out as described in Example 7 (b) except that instead of adding the ARM complexes to a panning tube biotinylated antigen was added directly to the translation mix after it had been diluted in ice-cold heparin buffer. The mixture was then incubated for 1 hour at 4° C., after which time biotinylated antigen along with associated ARM complexes was captured on streptavidin-coated magnetic beads (Dynal) which had been pre-blocked with heparin block solution (Example 7). Beads were washed, as described for the panning tubes, except they were not vortexed and after each wash the beads were pelleted on a magnet to allow removal of the supernatant. RNA was eluted from the beads with 200 µl elution buffer (2 mM EDTA, 1×TBS, Rnase inhibitor at 1U/µl), and RT-PCR, re-assembly and analysis carried out as described (Example 7).

c) Results i) H4 Library

The output of the selections was screened initially by ELISA to determine the percentage of clones selected that recognised the target antigen. For the H4 library after two rounds of panning the percentage of clones that were positive for binding to the antigen was 55%. 135 of these positive clones were picked and sequenced and were found to consist of 133 different sequences. These clones were all prepared as periprepes and ranked by off rate using BiaCore analysis. The five clones with the longest off rate as determined by this preliminary screen were then prepared as FPLC-purified monomeric scFv and accurate off rates determined. Results are shown in Table 3.

Two of the clones (B2B4 and B2H1) had improved off rates compared to the parental clone, demonstrating that the ribosome display selection regime described is useful for generation of affinity-improved variants by targeted mutagenesis.

ii) L4 Library

After four rounds of selection (2 panning and 2 using biotinylated antigen) 15% of the selected clones were positive for binding to the target antigen. 96 positive clones were taken for BiaCore anlaysis from the fourth round, and of these the five with the longest off rates were taken for further analysis. Results are shown in Table 4.

All five of the light chain CDR3 variants had improved off rates compared to the parental clone, again demonstrating the successful application of the ribosome display selection regime to generate improved variants by targeted mutagenesis.

EXAMPLE 9

Comparison of Structured Versus Unstructured Tethers in a Selection Format a) Introduction The degree of secondary structure associated with the tether of the ribosome display construct may influence the quantity and quality of antibodies generated by a ribosome display selection process. To assess this a comparison between a structured (bacteriophage gene III) tether and an unstructured (glycine-serine repeat) tether was performed using the H4 library described in Example as a model system.

b) Preparation of Input Template

PCR amplified H4 DNA template was used as input. The H4 scFv repertoire was amplified from the cloned H4 library (Example 8) using the primers mycseq10 and PEU. A glycine-serine tether was amplified from the ribosome display vector (FIG. 2) by PCR using the primers hismycback and HA tag. A gene III tether was generated by PCR using primers described in Hanes et al., 1999, FEBS letters 450, 105–110 with the addition of HA, his and myc tags, and the gene III-containing vector pCantab6 as template. Assembly and pull-through reactions were carried out as described in Example 3.

c) Selections

Two rounds of selection using immobilised antigen (GPI-linked cell surface receptor) were carried out as described previously (Example 7). Output was screened initially by ELISA to assess the number of positive clones generated by the selection process and a subset of clones were taken on for BiaCore analysis to determine the off rates.

d) Results

After two rounds of selection the percentage of clones that were positive for antigen binding by ELISA was 25% of the selections carried out using the gene III tether and 34% for the selections carried out using the GS tether. The off rates of 22 positive clones from each selection were measured as peripreps on the BiaCore. 36% of the positive clones from the gene III tether selection had improved off rates compared to the parental clone, whereas 40% of those from the GS selection were improved.

These results provide indication of the value of use of a glycine-serine tether in a ribosome display selection system in generating clones that bind antigen. A higher percentage of the clones selected using the GS tether (c.f. the gene III tether) were improved in terms of off rate compared to the parental clone. All the positive clones selected using either tether strategy have been sequenced and were found to be different suggesting the type of tether used does not affect the diversity of clones selected.

TABLE 1

Panel of scFv cloned into RDV1
Levels of expression were determined by SDS-PAGE analysis of $^{35}$S-Met labelled protein

| ScFv | $K_D$ (nM) | Antigen | Expression level |
|---|---|---|---|
| 1 | 8 | TGFβ-1 | ++ |
| 2 | 2 | TGFβ-2 | ++ |
| 3 | 0.3 | TNFα | ++ |
| 4 | 3.7 | Estradiol | ++ |
| 5 | 0.4 | IL-12 | +++ |
| 6 | 2.0 | IL-12 | +++ |
| 7 | 200 | IL-12 | +++ |
| 8 | 2000 | IL-12 | +++ |
| 9 | 3 | Fluorescein | +++ |
| 10 | ? | Fluorescein | ++ |
| 11 | ? | Fluorescein | + |
| 12 | ? | Fluorescein | ++ |

TABLE 2

Activity of the panel of scFv before and after adjustment of folding conditions

| ScFv | $K_D$ (nM) | Antigen | Activity -no refolding modifications | Activity modified folding |
|---|---|---|---|---|
| 1 | 8 | TGFβ-1 | − | + |
| 2 | 2 | TGFβ-2 | − | − |
| 3 | 0.3 | TNFα | − | + |
| 4 | 3.7 | Estradiol | − | − |
| 5 | 0.4 | IL-12 | + | + |
| 6 | 2.0 | IL-12 | − | + |
| 7 | 200 | IL-12 | − | +/− |
| 8 | 2000 | IL-12 | − | − |
| 9 | 3 | Fluorescein | + | + |
| 10 | ? | Fluorescein | + | + |
| 11 | ? | Fluorescein | + | + |
| 12 | ? | Fluorescein | − | − |

TABLE 3

| Clone | Mutagenesised sequence (VH CDR3) | $K_d$ (s$^{-1}$) | Fold improvement over parent |
|---|---|---|---|
| Parent | GWYAL (SEQ ID NO: 24) | 0.0203 | — |
| B1B3 | VNLLV (SEQ ID NO: 25) | 0.0233 | 0.87 |
| B1F12 | RSMDG (SEQ ID NO: 26) | 0.0283 | 0.71 |
| B2B4 | HAARR (SEQ ID NO: 27) | 0.0113 | 1.79 |
| B2H1 | RVRLL (SEQ ID NO: 28) | 5.9e-3 | 3.44 |
| B2B3 | FLSSI (SEQ ID NO: 29) | 0.0228 | 0.89 |

TABLE 4

| Clone | Mutagenised sequence (VL CDR3) | $K_d$ (s$^{-1}$) | Fold improvement over parent |
|---|---|---|---|
| Parent | DSSGN (SEQ ID NO: 30) | 0.0203 | — |
| C5 | SATHE (SEQ ID NO: 31) | 0.0166 | 1.2 |
| C10 | APHGS (SEQ ID NO: 32) | 0.0144 | 1.4 |
| A12 | TVNHD (SEQ ID NO: 33) | 0.0104 | 2.0 |
| D1 | HWQTD (SEQ ID NO: 34) | 7.4e-3 | 2.7 |
| H7 | NTSVT (SEQ ID NO: 35) | 2.5e-3 | 8.12 |

The invention claimed is:

1. A method of obtaining a specific binding pair (sbp) member that binds a complementary sbp member of interest, the method comprising:
   (a) providing mRNA molecules, each mRNA molecule comprising a nucleotide sequence encoding a specific binding pair member and lacking an in-frame stop codon;
   (b) incubating the mRNA molecules under conditions for ribosome translation of the mRNA molecules to produce encoded specific binding pair member, whereby complexes, each comprising ribosome, mRNA and encoded specific binding pair member displayed on the ribosome are formed;
   (c) bringing the complexes into contact with the complementary sbp member of interest, and selecting one or more complexes displaying specific binding pair member able to bind the complementary sbp member of interest under the conditions of the selection;
   wherein the mRNA molecules are incubated with prokaryotic ribosomes in a prokaryotic ribosome display system or are incubated with eukaryotic ribosomes in a eukaryotic ribosome display system;
   the method being characterised in that the mRNA molecules further comprise a sequence for encapsidation of the mRNA molecules in a viral coat, and the method comprises providing viral coat protein that recognises the sequence for encapsidation, thereby encapsidating mRNA comprised within complexes of mRNAs, ribosomes and displayed specific binding members in the viral coat protein co-translationally.

2. A method according to claim 1 wherein the mRNA molecules incorporate a Midvariant (MDV) RNA template enabling replication by Qβ replicase.

3. A method according to claim 1 wherein a gly-ser tether is fused C-terminally to specific binding pair member.

4. A method according to claim 3 wherein the gly-ser tether comprises 24 glycine-serine units.

5. A method according to claim 1 wherein oxidised and reduced glutathione is added at a ratio of between 1:1 and 10:1 after 30 minutes of ribosome translation.

6. A method according to claim 1 wherein protein disulphide isomerase (PDI) is employed in the incubation conditions, along with oxidised and reduced glutathione at a ratio of 1:1 and 10:1.

7. A method according to claim 1 wherein the translation system is eukaryotic and protein disulphide isomerase (PDI) is employed in the incubation conditions.

8. A method according to claim 1 comprising selecting for complexes comprising a specific binding member able to bind complementary specific binding member of interest, while blocking unspecific selection using heparin.

9. A method according to claim 1 wherein mRNA molecules for incubation in the translation system are provided by means of RT-PCR reactions in which at least one RT-PCR primer is a mutagenic primer encoding a diversity of different sequences for inclusion in a defined region of the nucleotide sequence encoding a specific binding pair member.

10. A method according to claim 1 wherein tobacco mosaic virus (TMV) viral coat protein and sequence for encapsidation ("origin assembly sequence"—"OAS") are employed.

11. A method according to claim 1 further comprising retrieving mRNA from a complex selected in step (c).

12. A method according to claim 11 wherein mRNA retrieved from a selected complex displaying a specific binding pair member (a "selected specific binding pair member") is amplified and copied into DNA encoding the selected specific binding pair member.

13. A method according to claim 12 wherein the DNA is provided in an expression system for production of a product, which product is the selected specific binding pair member or a polypeptide chain of the selected specific binding pair member.

14. A method according to claim 13 further comprising isolating or purifying the product.

15. A method according to claim 12 wherein DNA encoding the selected specific binding pair member or a polypeptide chain of the selected specific binding pair member is mutated to encode a polypeptide that comprises an amino acid sequence that differs from the selected specific binding pair member or polypeptide chain of the selected specific binding pair member.

16. A method according to claim 15 wherein mutated DNA encoding said polypeptide is provided in an expression system for production of a product, which product is said polypeptide.

17. A method according to claim 16 further comprising isolating or purifying the product.

* * * * *

SEQUENCE LISTING

<160> NUMBER OF SEQ ID NOS: 35

<210> SEQ ID NO 1
<211> LENGTH: 324
<212> TYPE: DNA
<213> ORGANISM: Artificial Sequence
<220> FEATURE:
<223> OTHER INFORMATION: Description of Artificial Sequence: Ribosome
      display construct

<400> SEQUENCE: 1
aattctaata cgactcacta tagggagagc acttctgatc cagtccgact gagaaggaag    60
gcccagccat ctgcagtacg cggccgcaca tcatcatcac catcacgggg ccgcagaaca   120
aaaactcatc tcagaagagg atctgaatgg ccgcggcagc gggtccggct ctgggagcgg   180
atccggctct gggagcggct ctgggtccgg atcgggctcc ggatcaggct cgggctccgg   240
atctggatcg ggctccggat ccgggtcggg ctccggatgg ggtcgggttc gggatcatac   300
ccgtatgacg tgccggatta cgca                                          324

<210> SEQ ID NO 2
<211> LENGTH: 76
<212> TYPE: DNA
<213> ORGANISM: Artificial Sequence
<220> FEATURE:
<223> OTHER INFORMATION: Description of Artificial Sequence: Primer

<400> SEQUENCE: 2
aattctaata cgactcacta tagggagagc acttctgatc cagtccgact gagaaggaag    60
gcccagccgg ccatgg                                                    76

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 3
tacccgtatg acgtgccgga ttacgca                                        27

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 4
taatacgact cactataggg agagcacttc tg                                  32

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 5
tgcgtaatcc ggcac                                                     15

<210> SEQ ID NO 6

-continued

```
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 6
ctcttctgag atgagttttt g                                              21

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 7
gcacatcatc atcaccatca cggggcc                                        27

<210> SEQ ID NO 8
<211> LENGTH: 135
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 8
tgcgtaatcc ggcacgtcat acgggtaact attttcccct ttgcggacat cactcttttt    60
tccggttcga gatcgaaact ttgcaagcct gatcgacata gggacatctt ccatgaactc   120
atcaacgact tcttc                                                   135

<210> SEQ ID NO 9
<211> LENGTH: 144
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 9
gaactcatca acgacttctt ctgtaagttc catgggccct ccgtctctca cgtttgtaat    60
cttctctctc aaaccattca gatcctcttc tgagatgagt ttttgttctg cggccccgtg   120
atggtgatga tgatgtcggg ccgc                                         144

<210> SEQ ID NO 10
<211> LENGTH: 147
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 10
gaactcatca acgacttctt ctgtaagttc catgggccct ccgtctctca cgtttgtaat    60
cttctctctc aaaccctaat tcagatcctc ttctgagatg agttttttgtt ctgcggcccc  120 gtgatggtga tgatgatgtc gggccgc                                      147

<210> SEQ ID NO 11
<211> LENGTH: 63
<212> TYPE: DNA
<213> ORGANISM: Artificial Sequence
<220> FEATURE:
```

-continued

<223> OTHER INFORMATION: Description of Artificial Sequence: 5' end of
      construct

<400> SEQUENCE: 11
ggggaccccc ccggaagggg gggacgaggt gcgggcacct cgtacgggag ttcgaccgtg    60
acg                                                                  63

<210> SEQ ID NO 12
<211> LENGTH: 156
<212> TYPE: DNA
<213> ORGANISM: Artificial Sequence
<220> FEATURE:
<223> OTHER INFORMATION: Description of Artificial Sequence: 3' end of
      construct

<400> SEQUENCE: 12
cacgggctag cgctttcgcg ctctcccagg tgacgcctcg tgaagaggcg cgaccttcgt    60
gcgtttcggt gacgcacgag aaccgccacg ctgcttcgca gcgtggctcc ttcgcgcagc   120
ccgctgcgcg aggtgacccc ccgaaggggg gttccc                             156

<210> SEQ ID NO 13
<211> LENGTH: 86
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 13
ggggaccccc ccggaagggg gggacgaggt gcgggcacct cgtacgggag ttcgaccgtg    60
acgaattcta atacgactca ctatag                                         86

<210> SEQ ID NO 14
<211> LENGTH: 106
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 14
tacccgtatg acgtgccgga ttacgcacac gggctagcgc tttcgcgctc tcccaggtga    60
cgcctcgtga agaggcgcga ccttcgtgcg tttcggtgac gcacga                  106

<210> SEQ ID NO 15
<211> LENGTH: 106
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 15
tcgtgcgtca ccgaaacgca cgaaggtcgc gcctcttcac gaggcgtcac ctgggagagc    60
gcgaaagcgc tagcccgtgt gcgtaatccg gcacgtcata cgggta                  106

<210> SEQ ID NO 16
<211> LENGTH: 96
<212> TYPE: DNA
<213> ORGANISM: Artificial Sequence
<220> FEATURE:
<223> OTHER INFORMATION: Description of Artificial Sequence:
      Oligonucleotide -continued

<400> SEQUENCE: 16
gcgtttcggt gacgcacgag aaccgccacg ctgcttcgca gcgtggctcc ttcgcgcagc      60
ccgctgcgcg aggtgacccc ccgaaggggg gttccc      96

<210> SEQ ID NO 17
<211> LENGTH: 96
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 17 gggaacccc cttcgggggg tcacctcgcg cagcgggctg cgcgaaggag ccacgctgcg      60
aagcagcgtg gcggttctcg tgcgtcaccg aaacgc      96

<210> SEQ ID NO 18
<211> LENGTH: 14
<212> TYPE: PRT
<213> ORGANISM: Homo sapiens

<400> SEQUENCE: 18

Asn Met Val Arg Gly Val Gly Arg Tyr Tyr Tyr Met Asp Val
 1               5                  10

<210> SEQ ID NO 19
<211> LENGTH: 11
<212> TYPE: PRT
<213> ORGANISM: Homo sapiens

<400> SEQUENCE: 19

Cys Ser Arg Asp Ser Ser Gly Tyr His Leu Val
 1               5                  10

<210> SEQ ID NO 20
<211> LENGTH: 10
<212> TYPE: PRT
<213> ORGANISM: Homo sapiens

<400> SEQUENCE: 20

Val His Asn Gly Trp Tyr Ala Leu Glu Tyr
 1               5                  10

<210> SEQ ID NO 21
<211> LENGTH: 11
<212> TYPE: PRT
<213> ORGANISM: Homo sapiens

<400> SEQUENCE: 21

Asn Ser Trp Asp Ser Ser Gly Asn His Val Val
 1               5                  10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Library
<221> NAME/KEY: SITE
<222> LOCATION: (4)..(8)
<223> OTHER INFORMATION: Xaa is any amino acid

<400> SEQUENCE: 22

```
Val His Asn Xaa Xaa Xaa Xaa Xaa Glu Tyr
1               5                   10
```

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Library
<221> NAME/KEY: SITE
<222> LOCATION: (4)..(8)
<223> OTHER INFORMATION: Xaa is any amino acid

<400> SEQUENCE: 23

```
Asn Ser Trp Xaa Xaa Xaa Xaa Xaa His Val Val
1               5                   10
```

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Mutagenized
      sequence

<400> SEQUENCE: 24

```
Gly Trp Tyr Ala Leu
1               5
```

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Mutagenized
      sequence

<400> SEQUENCE: 25

```
Val Asn Leu Leu Val
1               5
```

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Mutagenized
      sequence

<400> SEQUENCE: 26

```
Arg Ser Met Asp Gly
1               5
```

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Mutagenized
      sequence

<400> SEQUENCE: 27

```
His Ala Ala Arg Arg
1               5
```

<210> SEQ ID NO 28
<211> LENGTH: 5
<212> TYPE: PRT

-continued

```
<213> ORGANISM: Artificial Sequence
<220> FEATURE:
<223> OTHER INFORMATION: Description of Artificial Sequence: Mutagenized
      sequence

<400> SEQUENCE: 28

Arg Val Arg Leu Leu
 1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Mutagenized
      sequence

<400> SEQUENCE: 29

Phe Leu Ser Ser Ile
 1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Mutagenized
      sequence

<400> SEQUENCE: 30

Asp Ser Ser Gly Asn
 1               5

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Mutagenized
      sequence

<400> SEQUENCE: 31

Ser Ala Thr His Glu
 1               5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Mutagenized
      sequence

<400> SEQUENCE: 32

Ala Pro His Gly Ser
 1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Mutagenized
      sequence

<400> SEQUENCE: 33

Thr Val Asn His Asp
 1               5
```

```
<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Mutagenized
      sequence

<400> SEQUENCE: 34

His Trp Gln Thr Asp
  1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Mutagenized
      sequence

<400> SEQUENCE: 35

Asn Thr Ser Val Thr
  1               5
```